United States Patent [19]

Malfroy Camine et al.

[11] Patent Number: 5,262,178
[45] Date of Patent: Nov. 16, 1993

[54] THERAPEUTIC USE OF ENKEPHALINASE

[75] Inventors: Bernard Malfroy Camine, San Bruno; Daniel B. Borson, Pacifica; Jay A. Nadel, San Francisco, all of Calif.

[73] Assignee: Genentech, Inc., South San Francisco, Calif.

[21] Appl. No.: 668,372

[22] Filed: Mar. 11, 1991

Related U.S. Application Data

[63] Continuation of Ser. No. 366,352, Jun. 15, 1989, abandoned, which is a continuation of Ser. No. 117,779, Nov. 5, 1987, abandoned, which is a continuation of Ser. No. 2,473, Jan. 12, 1987, abandoned.

[51] Int. Cl.$^5$ .................. A61K 37/54; C12N 9/50
[52] U.S. Cl. ................... 424/94.67; 435/212
[58] Field of Search ............. 424/94.67; 435/212

[56] References Cited

PUBLICATIONS

Ehrenpreis, cited in Biol. Abstracts 75(5), ref. 36354 (1982).
Connelly et al, cited in Biol. Abstracts 81(11), ref. 98704 (1986).
Matsas et al, cited in Chem. Abstracts, 102:58258(f) (1985).
Stewart et al, cited in Chem. Abstracts 101:125753h (1984).
Borson et al., Physiologist 29:174 (1986).
Shore et al., Am. Rev. Respir. Dis. 137(2):331–336 (Feb. 1988).
Schwartz et al., Life Sciences 29:1715–1740 (1981).
Sekizawa et al., J. App. Physiol. 63(4):1401–1405 (1987).
Matsas, R. et al., Biochem. J. 223:433–440 (1984).
Connelly, J. C. et al. Proc. Natl. Acad. Sci. USA 82:8737–8741 (Dec. 1985).
Borson, D. B., et al., Experimental Lung Research 12:21–36 (1987).
Sekizawa, et al., J. Appl. Physiol, 63(4): 1401–1405 (1987).
Dusser, et al., J. Appl. Physiol, 65(6): 2585–2591 (1988).
Dusser, et al., The Journal of Pharmacology and Experimental Therapeutics, 244(2): 531–536 (1988).
Djokic, et al., J. Appl. Physiol, 66(5): 2338–2343 (1989).
Iwamoto, et al., Int. Arch. Allergy Appli. Immunol, 88:288–293 (1989).
Kohrogi, et al., J. Clin. Invest., 82:2063–2068 (1988).
Djokic, et al., The Journal of Pharmacology and Experimental Therapeutics, 248(1):7–11 (1989).
Djokic, et al., Am J. Physiol., 256:G39–G43 (1989).
Borson, et al., J. Appl. Physiol., 66(6):2653–2658 (1989).
Kohrogi, et al., J. Clin. Invest., 84:781–786 (1989).
Rubinstein, et al., Int. Arch Allergy Appl Immunol, 91:232–238 (1990).
Sheppard, et al., J. Clin Invest., 81:1111–1115 (1988).
Jacoby, et al., J. Appl Physiol., 64(6):2653–2658 (1988).
Dusser, et al., J. Appl. Physiol., 67(4):1504–1511 (1989).

*Primary Examiner*—Jacqueline Stone
*Attorney, Agent, or Firm*—Renee A. Fitts

[57] ABSTRACT

A method and therapeutic composition for the treatment of pathological disorders associated with endogenous peptides by the administration of enkephalinase or derivatives thereof.

18 Claims, 18 Drawing Sheets

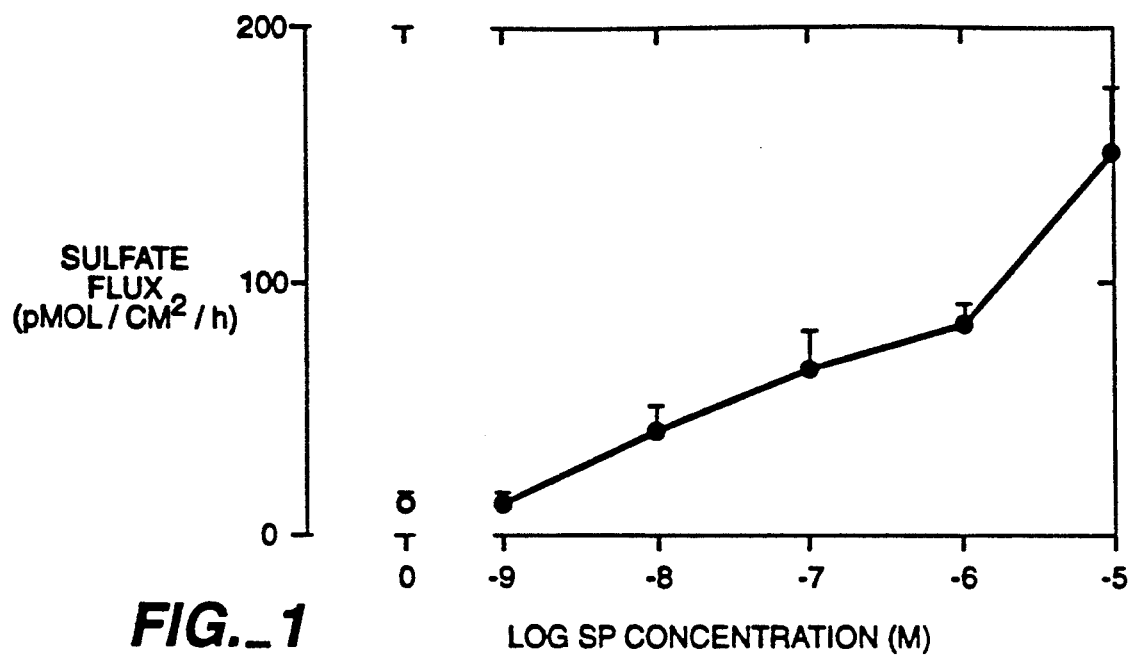
FIG._1
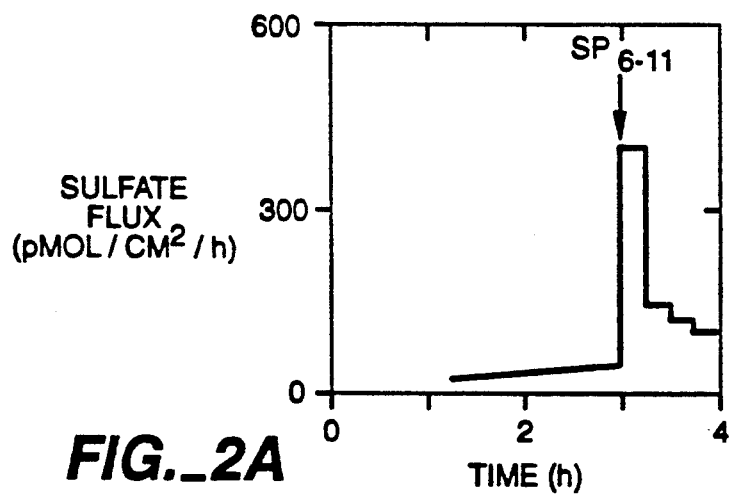
FIG._2A
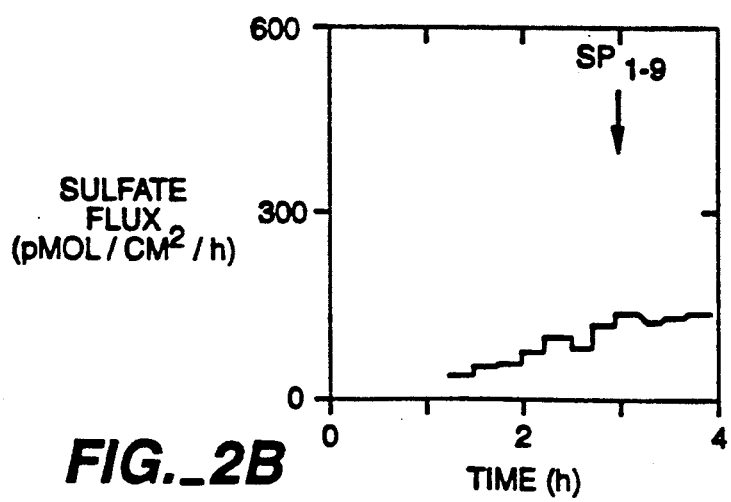
FIG._2B

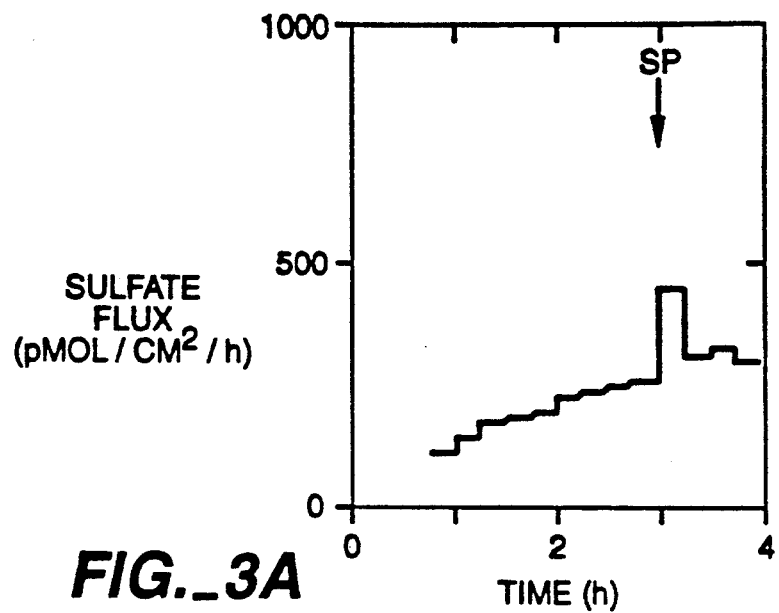
FIG._3A
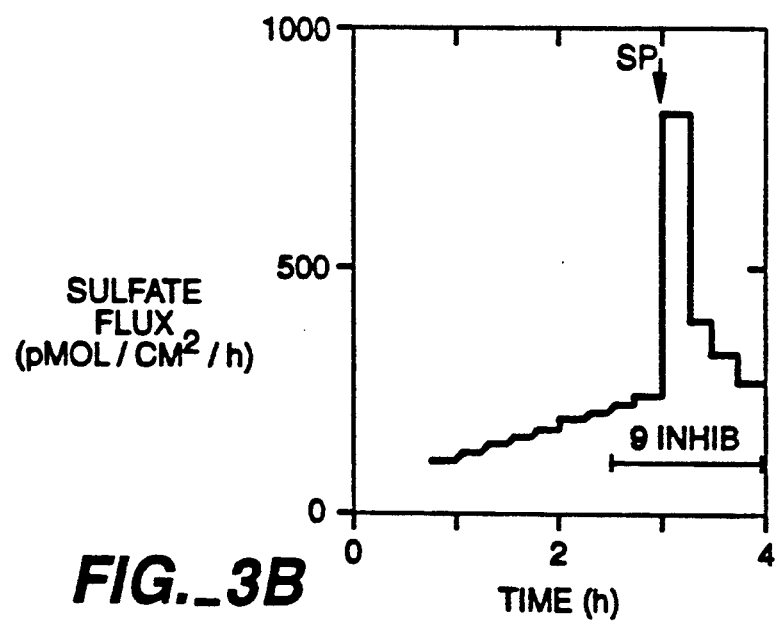
FIG._3B

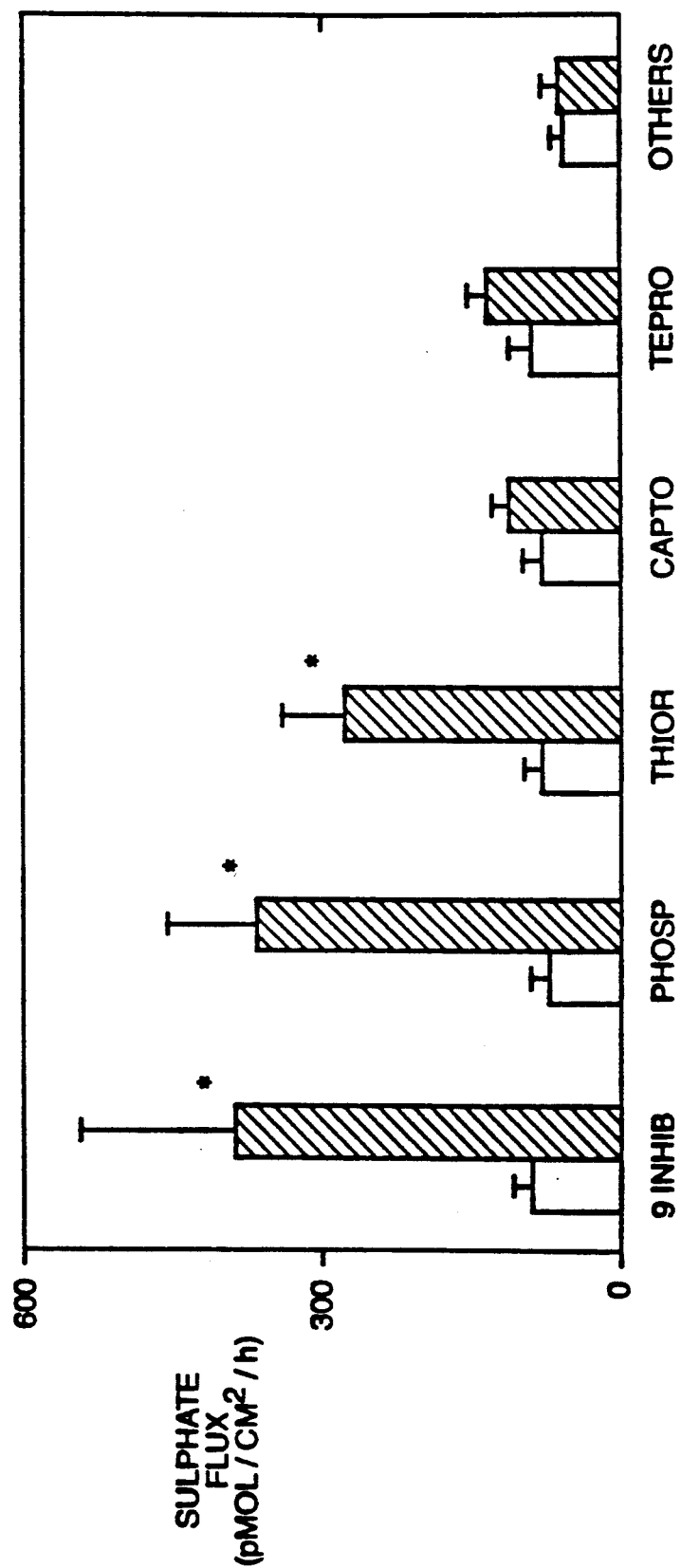
FIG._4

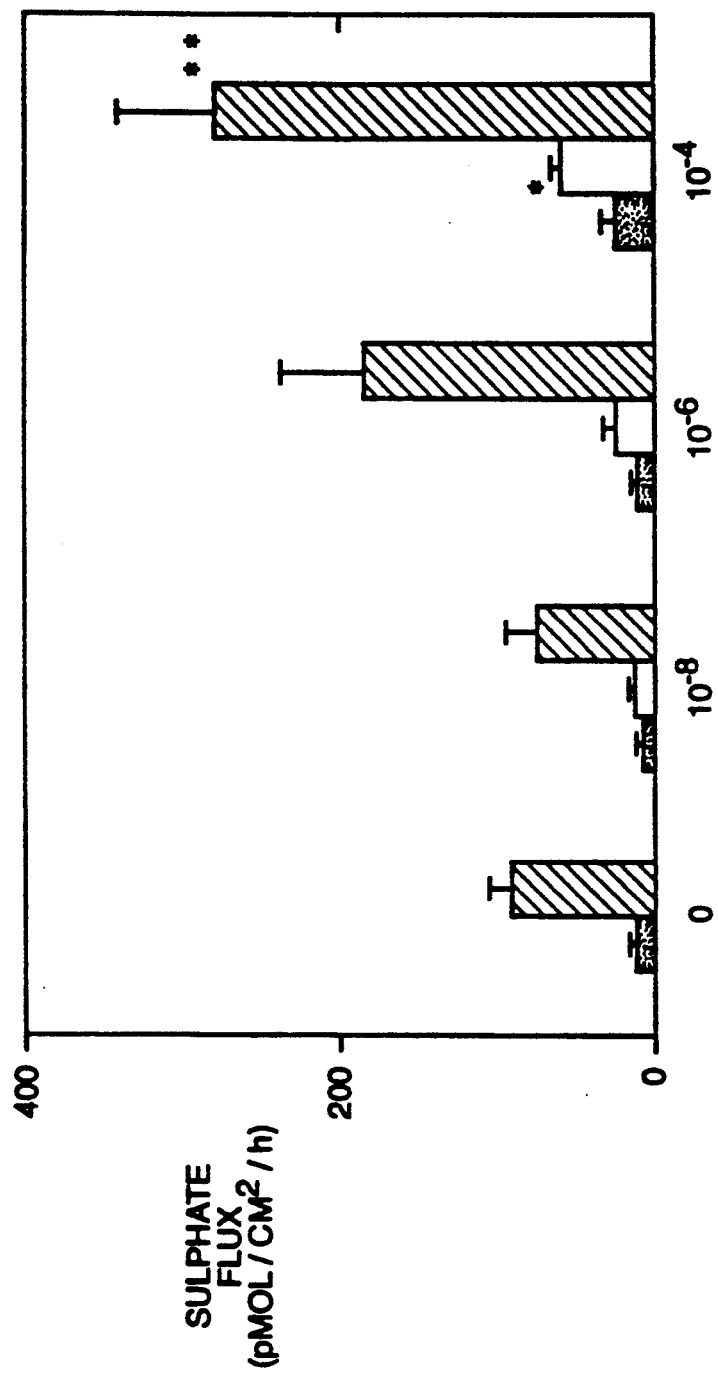
FIG._5

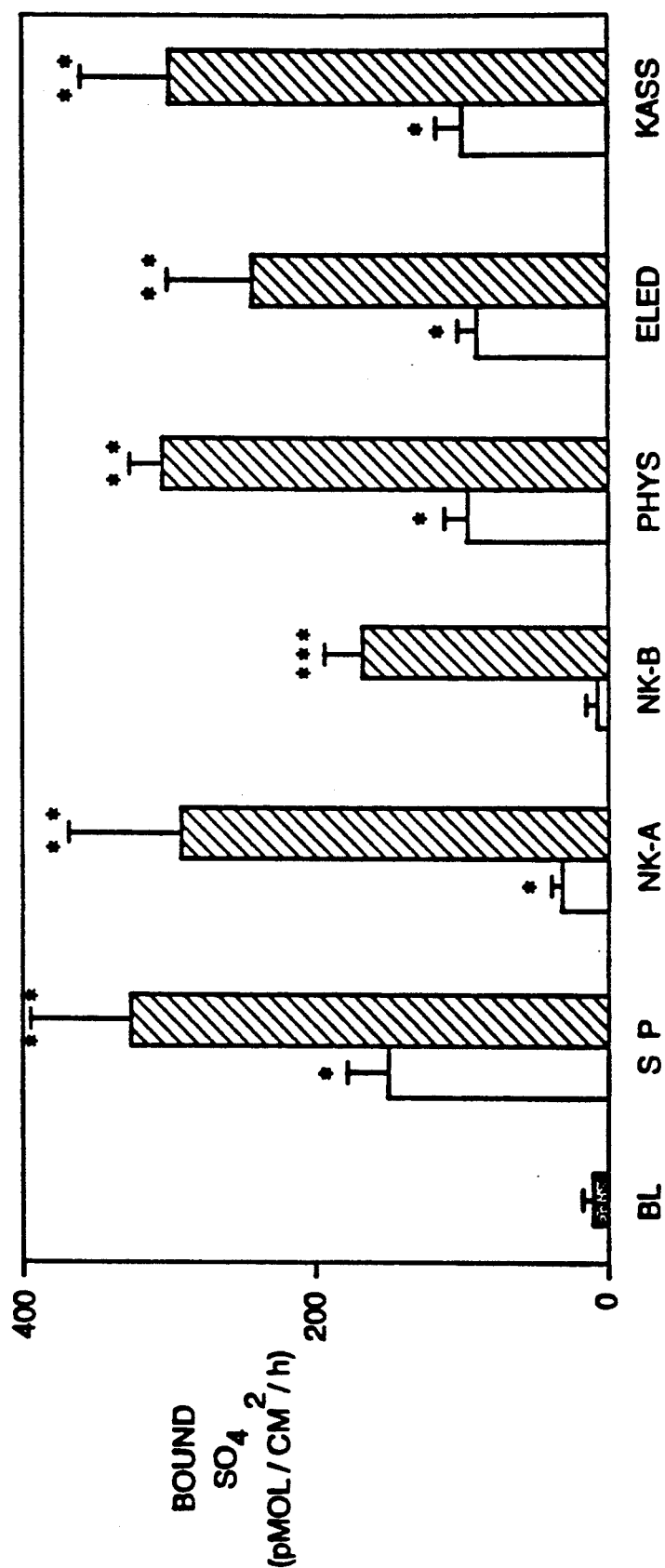
FIG._6

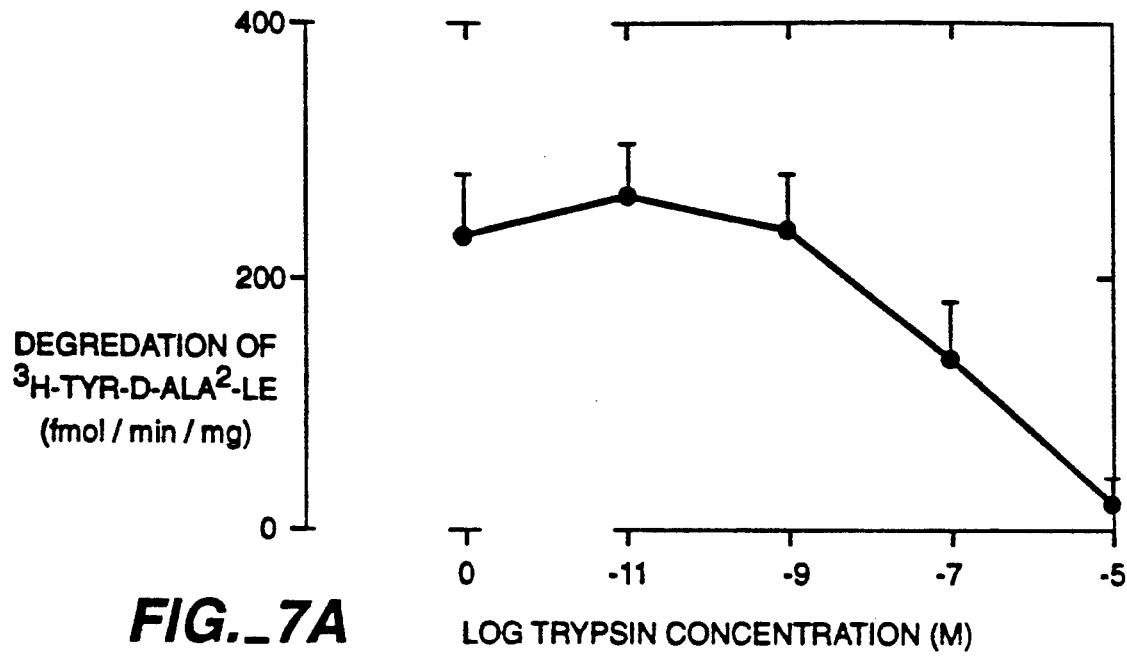
FIG._7A
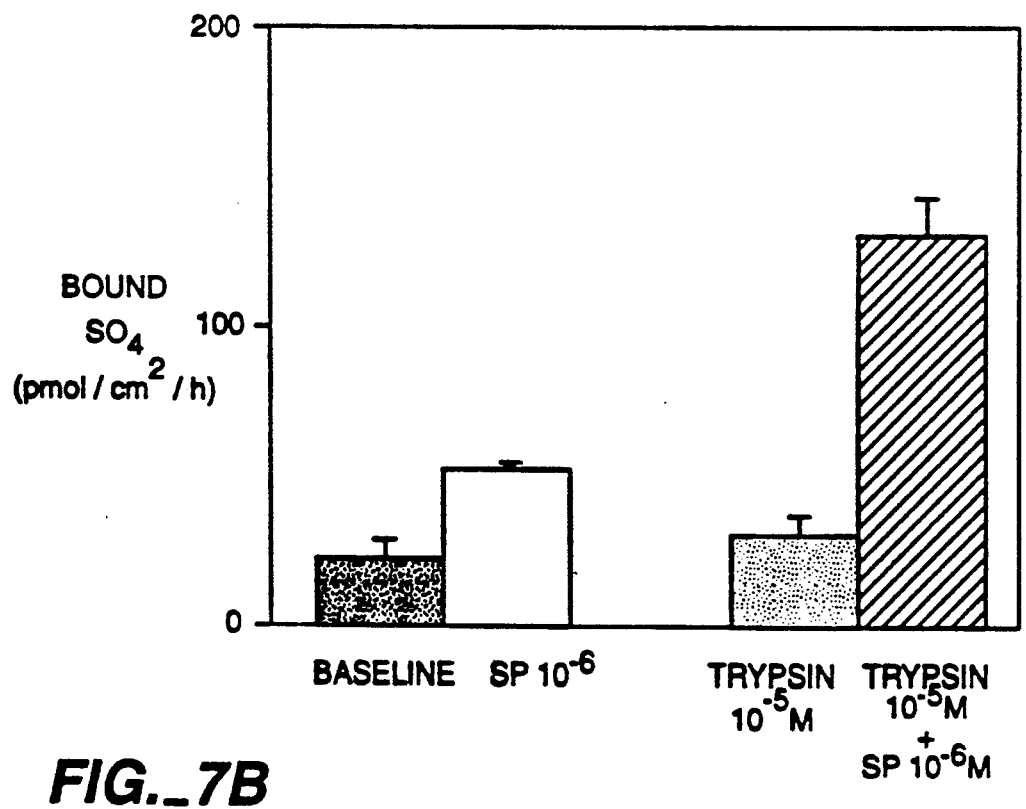
FIG._7B

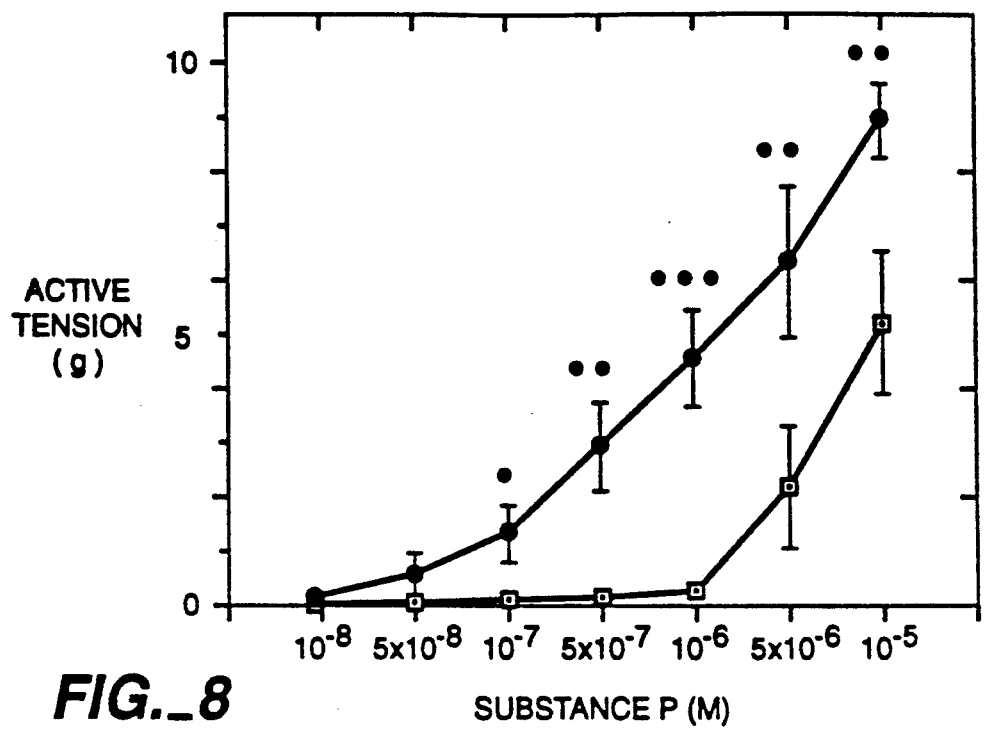
FIG._8
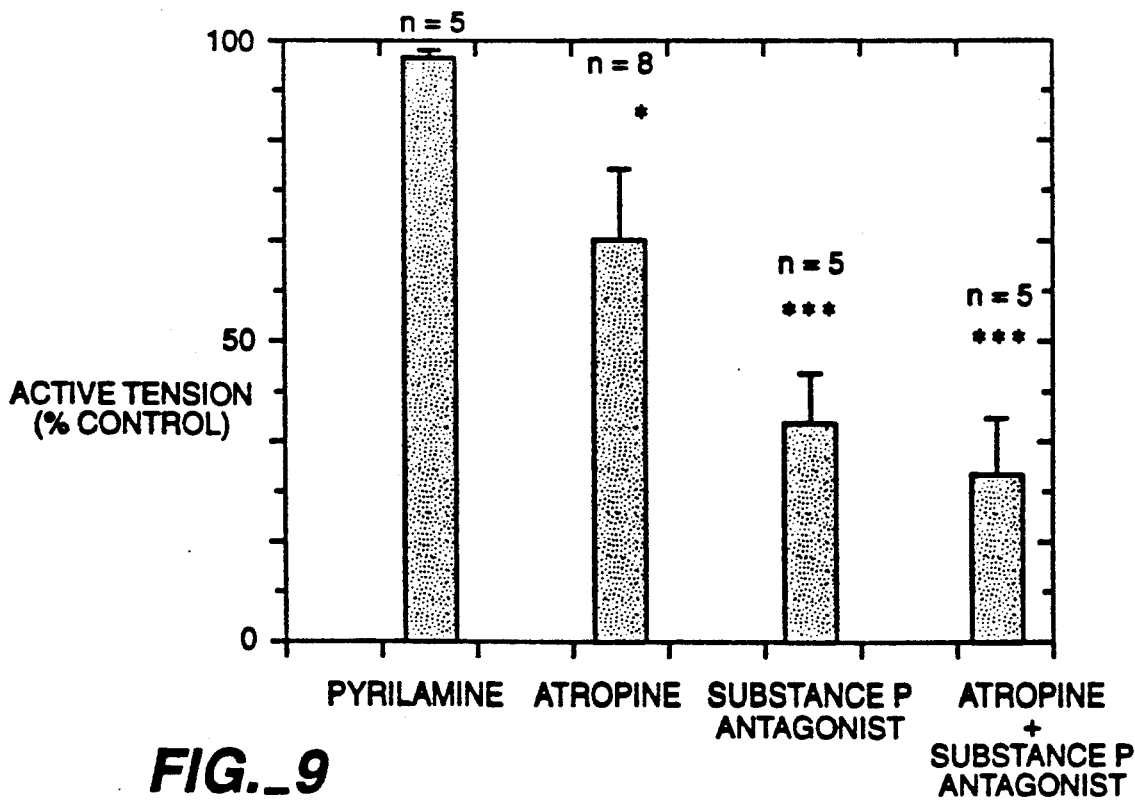
FIG._9

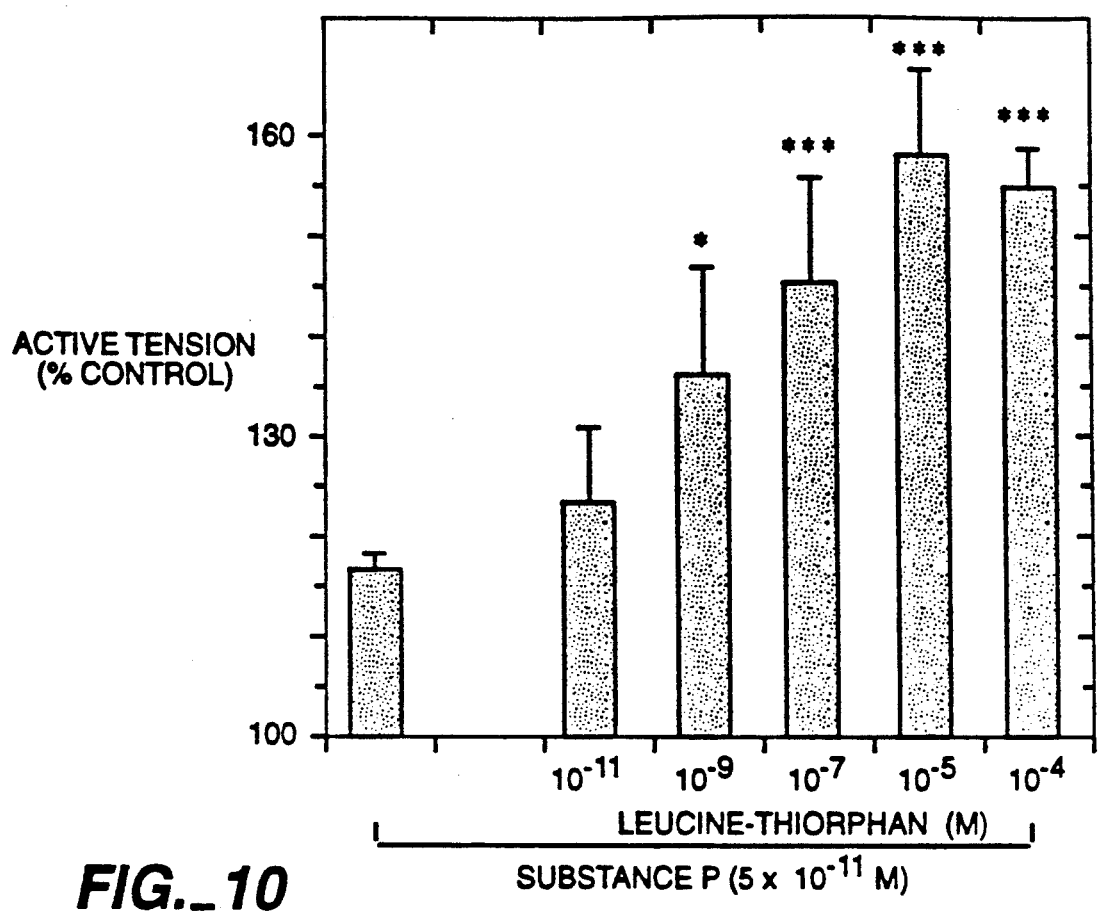
FIG._10
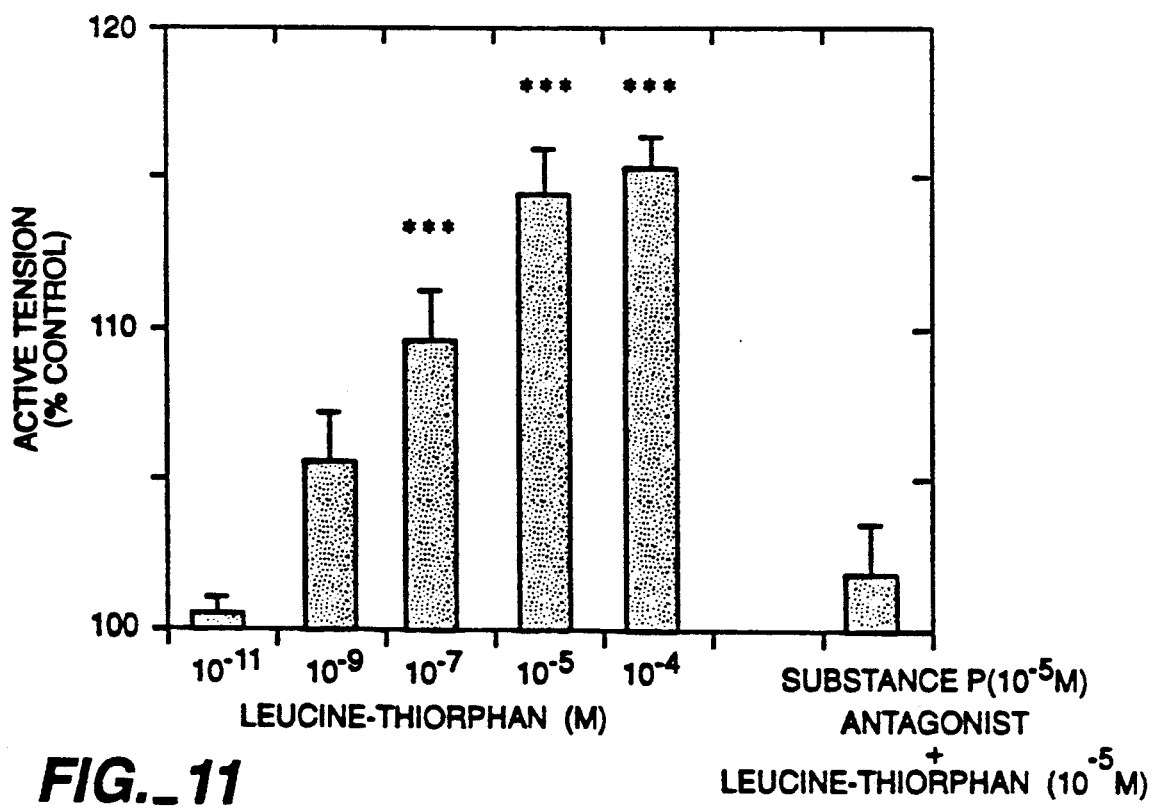
FIG._11

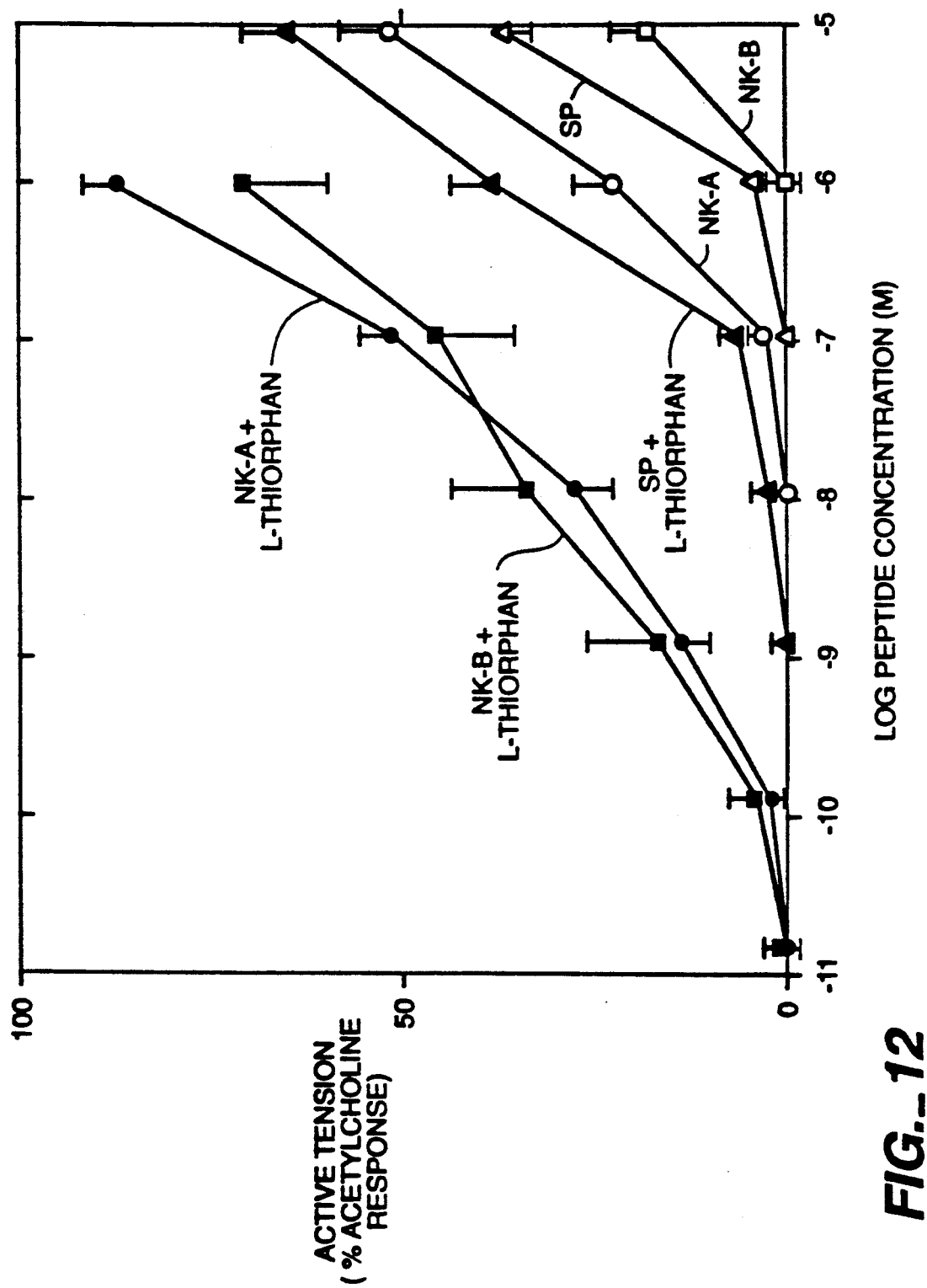
FIG._12

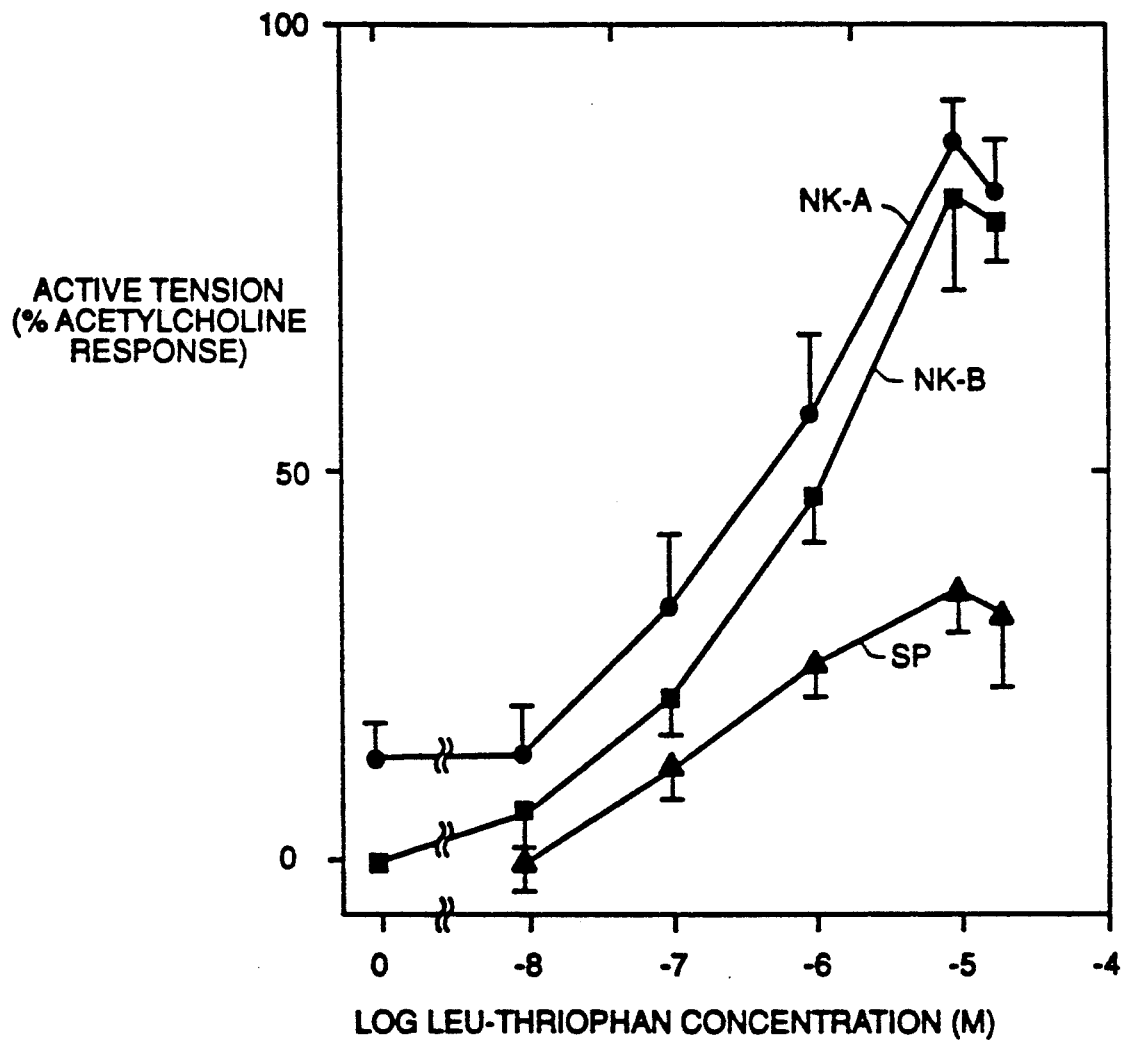
FIG._13

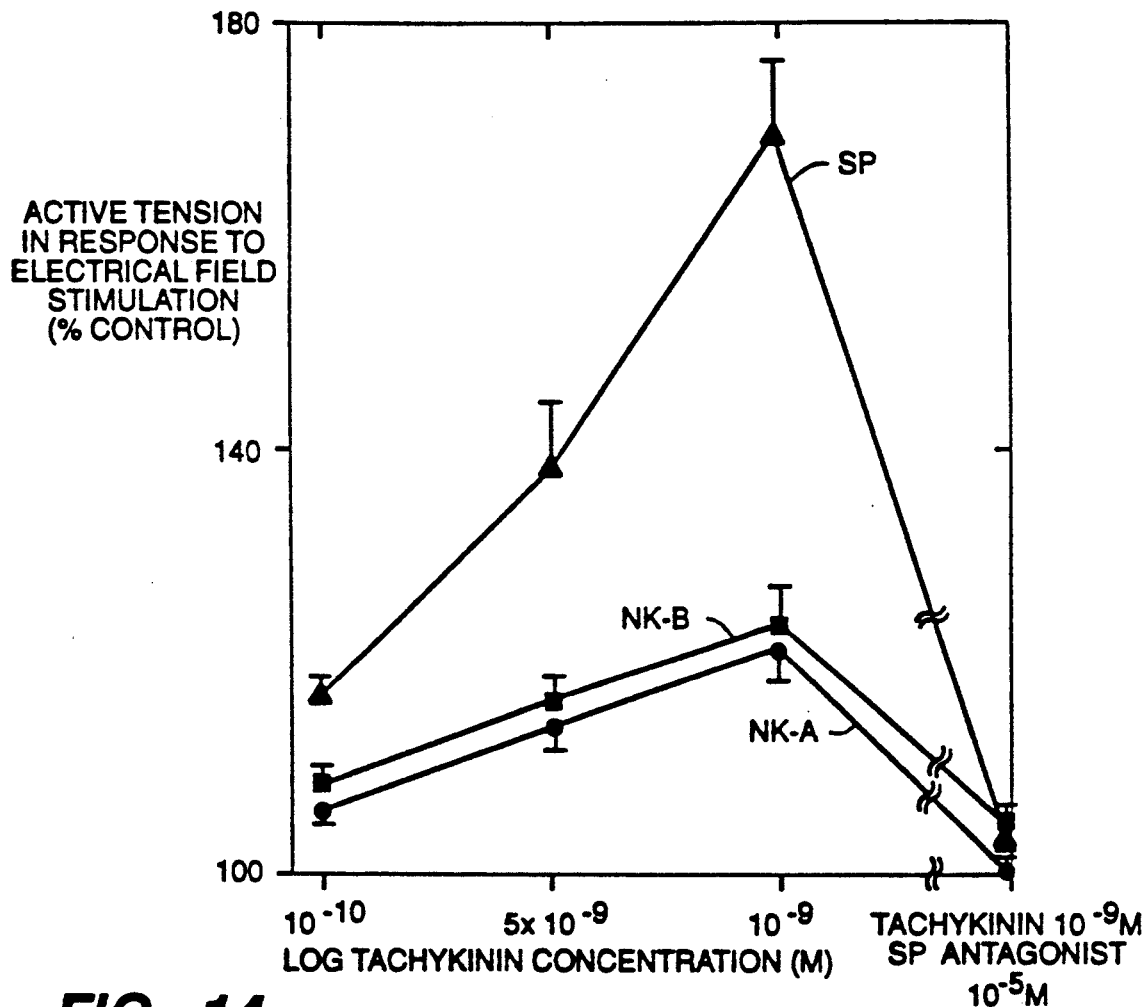
FIG._14

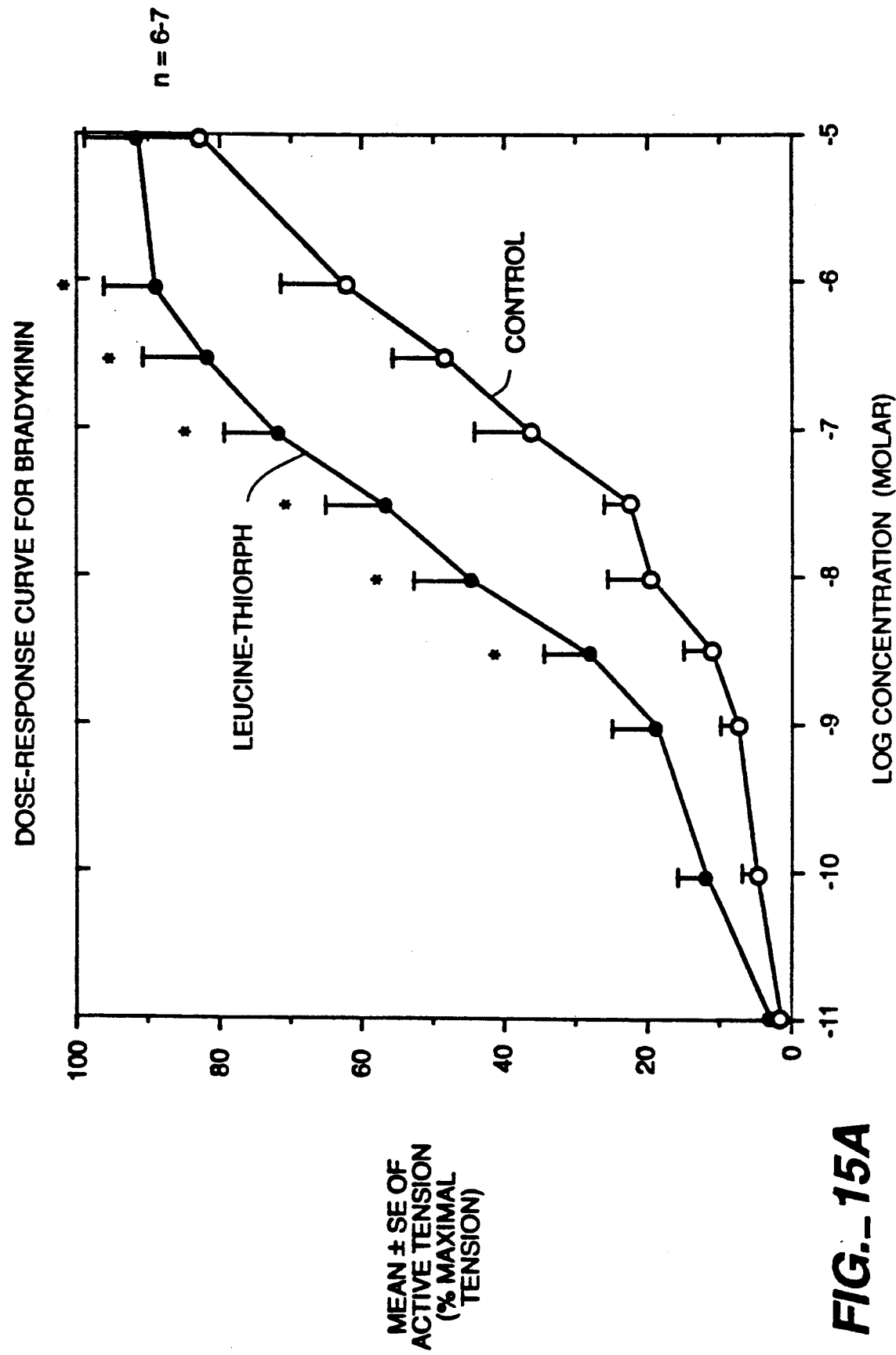
FIG._15A

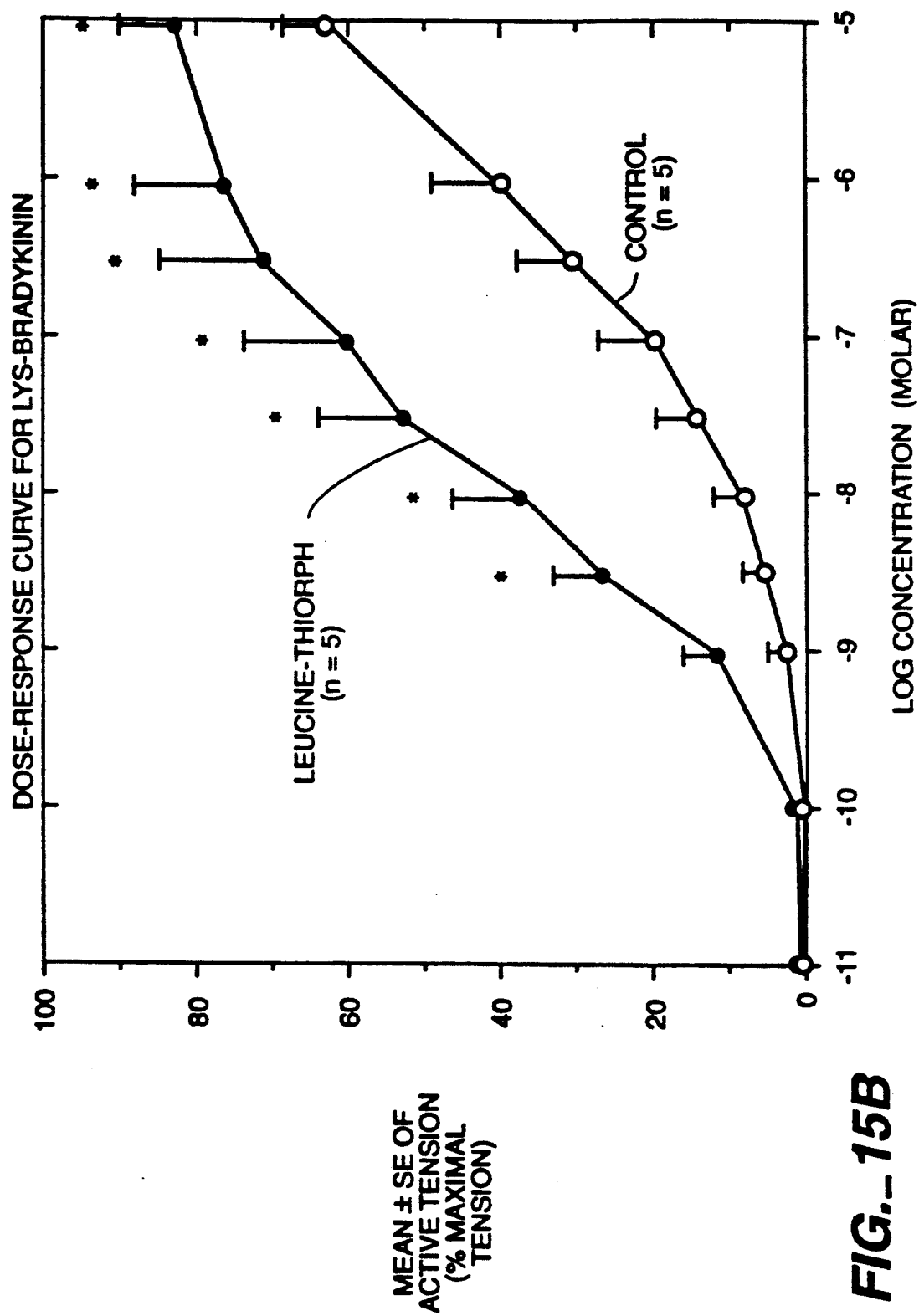
FIG._15B

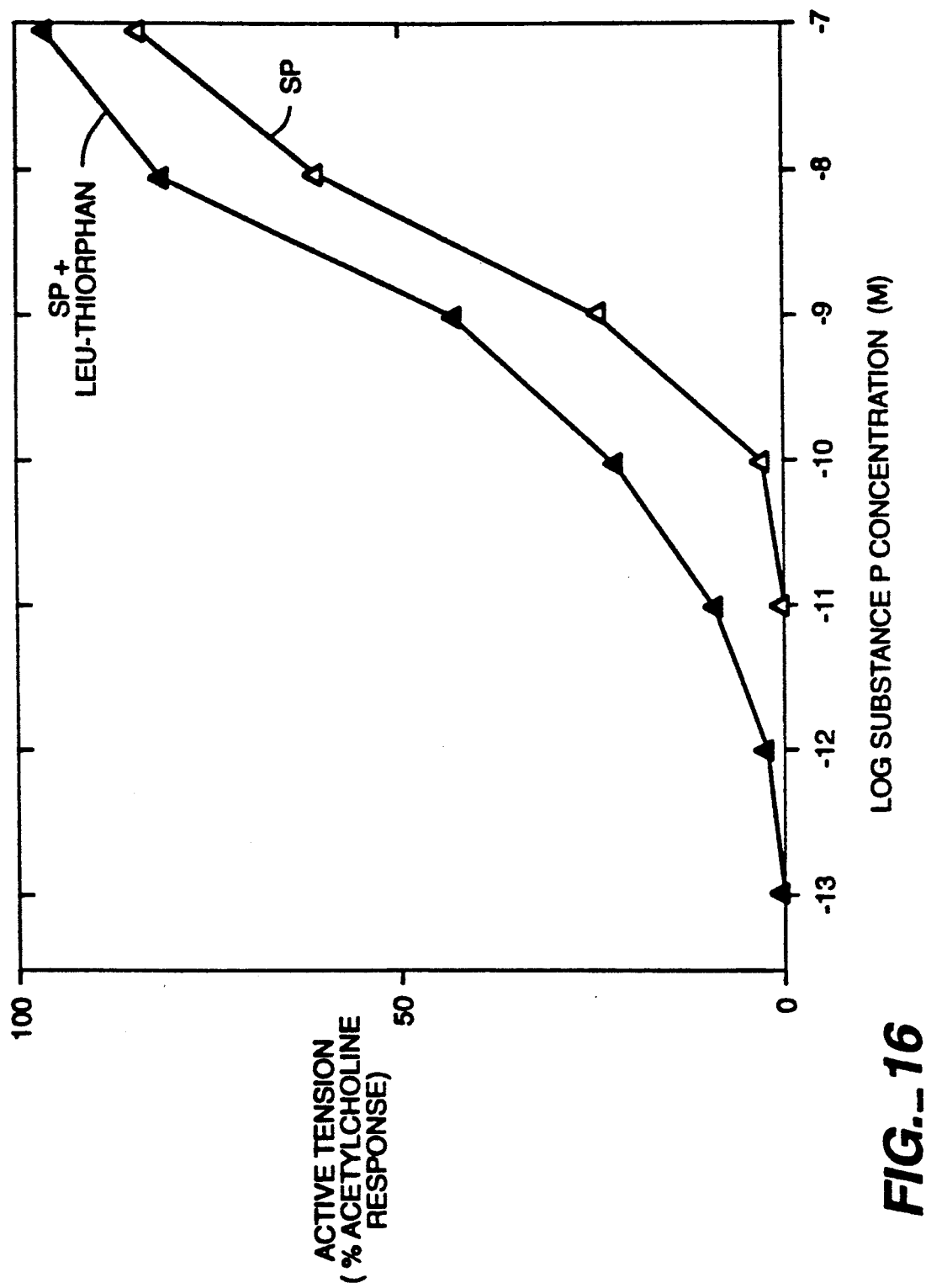
FIG._16

FIGURE 17(a)

[Figure shows a protein amino acid sequence of approximately 420+ residues, displayed in rows with position markers at every 10th residue (20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420). The sequence begins with Met Gly Arg Ser Glu... and continues through multiple rows of three-letter amino acid codes (Ser, Gln, Met, Asp, Ile, Thr, Asn, Ala, Pro, Lys, Arg, Trp, Leu, Glu, Val, Phe, Tyr, Cys, Gly, His).]

```
                                        430
Ala Phe Ala Gly Glu Ser Lys His Val Val Glu Asp Leu Ile Ala Gln Ile Ala Arg Glu Val Phe Ile Gln Thr Leu
            450                                 460                                 470
Asp Asp Leu Thr Trp Met Asp Ala Glu Thr Lys Lys Ala Glu Lys Tyr Leu Glu Leu Asn Lys Ala Ile Lys Arg Ile
                480                                 490                                 510
Gly Tyr Pro Asp Asp Ile Ile Ser Asn Glu Lys Leu Gln Asn Leu Lys Phe Ser Gln Ser Lys Tyr Leu Arg Glu Lys Val Glu Glu Val
    500                                 510                                 520
Glu Tyr Phe Glu Asn Ile Ile Ser Gly Ala Ala Val Val Asn Ala Phe Tyr Ser Ser Gly Arg Asn Gln Ile Val Phe
                530                                 540                                 570
Asp Lys Asp Glu Trp Ile Ser Gly Ala Ala Val Val Asn Ala Phe Tyr Ser Ser Gly Arg Asn Gln Ile Val Phe
    550                                 560                                 
Pro Ala Gly Ile Leu Gln Pro Phe Ser Ala Arg Gln Ser Asn Ser Leu Asn Tyr Gly Gly Ile Gly Met
                580                                 590
Val Ile Gly His Glu Ile Thr His Gly Phe Asp Asp Asn Gly Arg Asn Phe Asn Lys Asp Gly Asp Leu Val Asp
    600                                 610                                 620
Trp Trp Thr Gln Gln Ser Ala Asn Asn Phe Lys Asp Gln Ser Gln Cys Met Val Tyr Gln Tyr Gly Asn Phe Thr
                630                                 640
Trp Asp Leu Ala Gly Gly Gln Ile Leu Asn Gly Ile Asn Thr Leu Gly Glu Asn Ile Ala Asp Asn Gly Gly Ile
    650                                 660                                 670
Gly Gln Ala Tyr Arg Ala Tyr Gln Asn Tyr Val Lys Lys Asn Gly Glu Glu Lys Leu Leu Pro Gly Leu Asp Leu
                680                                 690
Asn His Lys Gln Leu Phe Phe Leu Asn Phe Ala Gln Val Trp Cys Gly Thr Tyr Arg Pro Glu Tyr Ala Val Asn
    700                                 710                                 720
Ser Ile Lys Thr Asp Val His Ser Pro Gly Asn Phe Arg Ile Ile Gly Thr Leu Gln Asn Ser Ala Glu Phe Ala
                730                                 740
Asp Ala Phe His Cys Arg Lys Asn Ser Tyr Met Asn Pro Glu Arg Lys Cys Arg Val Trp OP*

Protein sequence (residues 1–410+):

```
  1                                        10                                   
Lys Ser Glu Ser Gln Met Asp Ile Thr Asp Ile Asn Thr Pro Lys Lys Lys Gln Arg Trp Thr Pro
                                                                             20
Leu Glu Ile Ser Leu Ser Val Leu Val Leu Leu Thr Ile Ala Ala Thr Met Ile Ala Leu Tyr Ala Thr
 30                                       40                              
Tyr Asp Asp Gly Ile Cys Lys Ser Ser Asp Cys Ile Lys Ser Ala Ala Arg Leu Ile Gln Asn Met Asp Ala Thr
                  50                                        60                                   90
Thr Glu Pro Cys Thr Asp Phe Phe Lys Tyr Ala Cys Gly Gly Trp Leu Lys Arg Asn Val Ile Pro Glu Thr Ser
       70                                        80                              110
Ser Arg Tyr Gly Asn Phe Asp Ile Leu Arg Asp Glu Leu Val Val Leu Lys Asp Val Leu Gln Glu Pro Lys
           100                                       130                             140
Thr Glu Asp Ile Val Ala Val Gln Lys Ala Lys Ala Leu Tyr Arg Ser Cys Ile Asn Glu Ser Ala Ile Asp Ser
      120                              160
Arg Gly Gly Glu Pro Leu Leu Lys Leu Leu Pro Asp Ile Tyr Gly Trp Pro Val Ala Thr Glu Asn Trp Glu Gln
 150                                      190
Lys Tyr Gly Ala Ser Trp Thr Ala Glu Asp Lys Ile Ala Gln Leu Asn Ser Lys Tyr Gly Lys Lys Val Leu Ile
    170                              210
Asn Leu Phe Val Gly Thr Asp Asp Lys Asn Ser Val Asn His Val Ile Ala Gln Leu Pro Arg Leu Gly Leu
       180                              240
Pro Ser Arg Asp Tyr Tyr Glu Cys Thr Gly Ile Tyr Lys Glu Ala Cys Thr Ala Tyr Val Asp Phe Met Ile Ser
    200                              260
Val Ala Arg Leu Ile Arg Gln Glu Glu Leu Ile Ala Asn Ala Leu Pro Ile Asp Glu Asn Leu Ala Leu Glu Met
    220                              290
Met Glu Leu Glu Lys Glu Lys Ile Leu Ala Asn Ala Thr Leu Lys Pro Glu Asp Arg Asn Asp Pro Met Leu Tyr Asn
    270                              300                              310
Lys Met Thr Leu Ala Gln Ile Leu Gln Asn Asn Phe Ser Leu Glu Ile Asn Gly Lys Pro Phe Ser Trp Leu Asn Phe
      320                              340
Thr Asn Glu Ile Met Ser Thr Val Asn Ile Ser Ile Thr Asn Glu Glu Asp Val Val Tyr Ala Pro Glu Tyr
      330                              360
Leu Thr Lys Leu Lys Pro Ile Leu Thr Lys Tyr Ser Ala Arg Asp Leu Gln Asn Leu Met Ser Trp Arg Phe Ile
      350                              390
Met Asp Leu Val Ser Ser Leu Ser Arg Thr Tyr Lys Glu Ser Arg Asn Ala Phe Arg Lys Ala Leu Tyr Gly Thr
      370                              380                              410
Thr Ser Glu Thr Ala Thr Trp Arg Arg Cys Ala Asn Tyr Val Asn Gly Ala Asn Met Glu Asn Ala Val Gly Arg Leu
                                       400
```

FIGURE 18(b)

```
                                                                  440
Tyr Val Glu Ala Ala Phe Ala Gly Glu Ser Lys Val His Val Glu Asp Leu Ile Ala Gln Ile Ala Arg Glu Val Phe
420                                                 430                        460
Ile Gln Thr Leu Asp Asp Leu Thr Trp Met Asp Ala Glu Thr Lys Lys Arg Ala Glu Glu Lys Ala Leu Ala Ile
470                                                 480                        490
Lys Glu Arg Ile Gly Tyr Pro Asp Asp Ile Val Ser Asn Asp Asn Lys Leu Asn Asn Glu Tyr Leu Glu Leu Asn
500                                                 510
Tyr Glu Asp Glu Tyr Phe Glu Asn Ile Ile Gln Asn Leu Lys Phe Ser Gln Ser Lys Gln Ser Lys Lys Lys Leu
520                                                 530                        540
Arg Gly Lys Val Asp Lys Asp Trp Ile Ser Gly Ala Ala Val Asn Ala Phe Tyr Ser Ser Gly Arg Asn
550                                                 560
Gln Ile Val Phe Pro Ala Gly Ile Leu Gln Pro Phe Ser Ala Gln Gln Ser Asn Ser Leu Asn Tyr Gly
570                                                 580                        590
Gly Ile Gly Met Val Ile His Glu Ile Thr His Gly Phe Asp Asp Asn Gly Arg Asn Phe Asn Lys Asp Gly
600                                                 610
Asp Leu Val Asp Trp Trp Thr Gln Gln Ser Ala Sre Asn Phe Lys Glu Gln Ser Gln Cys Met Val Tyr Gln Tyr
620                                                 630                        640
Gly Asn Phe Ser Trp Asp Leu Ala Gly Gly Gln His Leu Asn Gly Ile Asn Thr Leu Gly Glu Asn Ile Ala Asp
650                                                 660
Asn Gly Gly Leu Gly Gln Ala Tyr Arg Ala Tyr Gln Asn Tyr Ile Lys Lys Asn Gly Glu Glu Lys Leu Leu Pro
670                                                 680                        690
Gly Leu Asp Leu Asn His Lys Gln Leu Phe Phe Leu Asn Phe Ala Gln Val Trp Cys Gly Thr Tyr Arg Pro Glu
700                                                 710
Tyr Ala Val Asn Ser Ile Lys Thr Asp Val His Ser Pro Gly Asn Phe Arg Ile Ile Gly Thr Leu Gln Asn Ser
720                                                 730                        740
Ala Glu Phe Ser Glu Ala Phe His Cys Arg Lys Asn Ser Tyr Met Asn Pro Glu Lys Lys Cys Arg Val Trp OP*
```

THERAPEUTIC USE OF ENKEPHALINASE

This invention, in part, was made with government support under Grant HL24136 with the National Institutes of Health and the University of California. The Government has certain rights in a part of this invention.

This is a continuation of co-pending application Ser. No. 07/366,352, filed Jun. 15, 1989 which is a continuation of Ser. No. 117,779, Nov. 5, 1987, which is a continuation of Ser. No. 2,473, Jan 12, 1987, all now abandoned.

BACKGROUND

The present invention relates to the treatment of pathological conditions associated with various endogenous peptides. In particular, the invention relates to the use of enkephalinase (E.C. 3.4.24.11) and novel forms thereof in such treatment.

Various endogenous peptides have been discovered which appear active in various physiological systems. For example, two pentapeptides, referred to as enkephalins, were extracted from the brain. The effects of enkephalins include analgesia, thermoregulation, tranquilization, gastrointestinal function and increasing appetite. Until the present invention, the sole physiological activity of enkephalinase was thought to be the cleavage of enkephalins in the central nervous system (Schwartz, J. C. et al., Trends Pharmacol Sci. 6: 472-476 [1985]). which to date is not known to be associated with any pathological disorder. Because such activity would result in an enhancement of pain, scientific research has focused on inhibiting enkephalinase. This invention establishes therapeutic uses of enkephalinase for the first time.

Another endogenous peptide, angiotensin II, is presumed to be an etiologic agent in the pathological condition of renal hypertension. Bradykinin and kallidin have been associated with other pathological conditions such as acute inflammation associated with burns, rheumatoid arthritis, edema, carcinoid syndrome, pancreatitis, migraine headache, reactions after transfusion with plasma products, allergic diseases, endotoxic shock and anaphylactic shock.

Another class of endogenous peptides are the tachykinins which share some of the same physiological activity. The tachykinins include substance P, eledoisin, neurokinin A and B, physalaemin and kassinin Substance P has been shown to be associated with smooth muscle contraction, neurotransmission, pain, cough, exocrine secretion, vasodilation, increased vascular permeability, increased adherence of leukocytes to venules, stimulation of polymorphonuclear leukocytes, macrophages, T lymphocytes, and degranulation of mast cells. Endogenous peptides such as bombesin have been found to be present in endocrine cells in normal lungs (Cutz et al., Experientia 37, 765-767 [1981]), released from carcinoid tumors, and implicated in the associated cutaneous flushes, telangiectasia, diarrhea and bronchoconstriction.

Bombesin functions as a growth factor for airway epithelial cells (Willey et al., Exp. Cell Res. 153, 245-248 [1984]) and for human small-cell lung cancer (Cuttitta, F. et al., Nature 316, 823-826 [1985]). Substance P and bombesin, apart from their tumor-associated effects, have been shown to contract the pulmonary artery and the airways. In light of the observations of the instant invention these endogenous peptides may mediate various pathophysiologic states including bronchial asthma and hypoxic pulmonary vasoconstriction. Some peptides are chemotactic, e.g. eosinophil chemotactic factor, $C_{3a}$ and substance P. They are generated at the site of inflammation and attract various immunological cells including neutrophils to the site. Finally, other peptides such as cholecystokinin, somatostatin, oxytocin and caerulin have potent effects on various tissues which may give rise to other pathological disorders.

Enkephalinase has been purified from kidney (Kerr, M. A. and Kenny, A. J. Biochem. J. 137: 477-488 [1974], Gafford. J. et al., Biochemistry 22, 3265-3271 [1983] and Malfroy. B. and Schwartz, J. C. Life Sci 31, 1745-1748 [1982]), intestine (Danielsen, E. M. et al., Biochem. J. 191, 545-548 [1980]), pituitary (Orlowski, M. and Wilk, S. Biochemistry 20: 4942-4945 [1981]), brain (Relton, J. M. et al., Biochem. J. 215: 755-762 [1983]) and lymph nodes (Bowes, M. A. and Kenny, A. J., Biochem. J. 236: 801-810 [1986]). Enkephalinase has been detected in many peripheral organs (Llorens. C. and Schwartz. J. C., Eur. J. Pharmacol. 69, 113-116 (1981) and in human neutrophils (Connelly, J. C. et al., Proc. Natl. Acad. Sci.[USA] 82: 8737-8741 [1985]). The distribution of enkephalinase in the brain closely parallels that of the enkephalins (Llorens, C. et al., J. Neurochem. 39: 1081-1089 [1982]). The observations of the instant invention establish that enkephalinase is also present in those peripheral tissues and cells that respond to endogenous peptides. Enkephalinase is a membrane-bound glycoprotein with subunit $M_r$ values in the range of 87,000 to 94,000. Variation in the $M_r$ values is attributed to differences in the extent and pattern of glycosylation.

The substrate specificity of enkephalinase has been studied using the enzyme from rat and human kidney. Malfroy, B. and Schwartz, J. C., J. Biol. Chem. 259: 14365-14370 (1984); Gafford et al., Biochemistry 22: 3265-3271 (1983); and Pozsgay, M. et al., Biochemistry 25: 1292-1299 (1986). These studies indicate that enkephalinase preferentially hydrolyzes peptide bonds comprising the amino group of a hydrophobic residue, shows a marked preference for short peptides, and is most efficient when it acts as a dipeptidyl carboxypeptidase releasing a carboxy terminal dipeptide. Enkephalinase, which had been found in cerebral synaptic membranes, efficiently cleaves the $Gly^3$-$Phe^4$ amide bond of enkephalins (Malfroy, B. et al., Nature (Lond.) 276: 523-526 [1978]). Enkephalinase has also been found to cleave the heptapeptide (Met[5])enkephalin-$Arg^6$-$Phe^7$ (Schwartz, J. C. et al., In Proceedings International Union of Pharmacology 9th Congress of Pharmacology, 3: ed. by J. F. Mitchell et al., 277-283, McMillan Press Ltd., London, [1984]) as well as a variety of other neuropeptides, such as cholecystokinin (Zuzel, K. A. et al., Neuroscience 15: 149-158 [1985]), substance P (Horsthemke, B. et al. Biochem. Biophys. Res. Comm. 125: 728-733 [1984]), neurotensin (Checler et al., 1983), angiotensin I and angiotensin II (Matsas et al., Biochem J. 223 433 [1984] and Gafford et al., Biochemistry 22: 3265 [1983]), kinins, e.g. bradykinin (Gafford. J. T. et al., Biochemistry 22 3265-3271 [1983]), oxytocin (Johnson et al., 1984), and somatostatin (Mumford, R. A. et al., Proc. Natl. Acad. Sci [USA] 78:6623-6627 [1981]). While enkephalinase is capable of hydrolyzing many biological peptides in vitro (Kenny, A. J. Trends in Biochem. Sci. 11: 40-42 [1986]), in vivo enkephainase has to date only been implicated in the hydrolysis of endogenous enkephalins when released in brain (Schwartz, J. C. et al., Life Sciences 29: 1715-1740 [1981] and Lecomte, J. M. et al., J. Pharmacol Exp. Ther. 237: 937-944 [1986]). Although the levels of enkephalinase in blood are normally very low (Connelly et al., supra) enkephalinase was found to be present in high levels in the serum from patients with adult respiratory distress syndrome (Connelly et al. Supra). Enkephalinase cleaves the chemotactic tripeptide fMet-Leu-Phe. Id. It was also observed that neutrophils from donors who smoked had enkephalinase activites about twice that of nonsmokers. Id. Enkephalinase has also been found in high levels in the microvilli of human placentae (Johnson, A. R. et al., Peptides 5: 789-796 [1984]).

The present invention is based on the novel observations that specific inhibitors of enkephalinase, thiorphan, leucine-thiorphan and phosphoramidon, potentiate airway mucus secretion and smooth muscle contraction induced by endogenous peptides, e.g. substance P and other tachykinins, and kinins such as bradykinin. The invention is also based on the novel observation that in vivo enkephalinase inhibits substance P-induced increases in vascular permeability. Enkephalinase is known to cleave substance P into two fragments observed to be ineffective in stimulating mucus secretion and/or smooth muscle contraction. The invention is also based on the observation that enkephalinase digests chemotactic molecules and thus may inhibit the attraction of various inflammatory cells including neutrophils to the site of injury.

An object of the present invention is to provide a therapeutic composition for the treatment of pathological conditions in which endogenous peptides may be involved. Specifically, enkephalinase may be used as a therapeutic agent to overcome adverse effects of substance P or other neuropeptides. More specifically, enkephalinase may be used to reduce peptide-mediated mucus secretion and bronchoconstriction in the airway consequent to various diseases e.g. asthma, chronic bronchitis, cystic fibrosis, and viral infections. Enkephalinase may also be used as a therapeutic agent in the treatment of various tumors, e.g. carcinoid tumors and small cell carcinoma of the lung. Yet another object of this invention is the use of enkephalinase derivatives in the treatment of various pathological disorders mediated by certain endogenous peptides. Other peptide-induced disorders may arise in the gastrointestinal, visual, urinary, circulatory, reproductive systems and joints. The cytoplasmic and/or transmembrane deleted or substituted enkephalinase may be used in the treatment of various pathological disorders mediated by certain endogenous peptides.

SUMMARY OF THE INVENTION

The present invention is based on the novel observations that the effects of endogenous peptides such as substance P and other tachykinins, and/or bradykinin on mucus secretion and smooth muscle contraction in airways are potentiated by specific enkephalinase inhibitors. The invention is directed to the administration of therapeutic compositions comprising enkephalinase or derivatives thereof for the treatment of certain pathological disorders mediated by various endogenous peptides, for example. bronchoconstriction, airway hypersecretion, acute inflammation or hyperimmune responses, systemic hypertension, cough, infertility or cancer.

BRIEF DESCRIPTION OF THE DRAWINGS

FIG. 1. Concentration-dependence of substance P (SP)-induced secretion (mean±SE), measured as release of $^{35}SO_4$-labeled macromolecules (sulfate flux). Tissues from 6 ferrets were incubated with SP at the concentrations indicated, and the change in sulfate flux for each tissue was calculated by subtracting the flux of bound $SO_4$ for the sample collected immediately before adding SP from the flux of bound $SO_4$ for the sample collected either 15 or 30 min after adding SP, whichever was greater. The average change in baseline secretion (B) over the 15 min prior to adding SP is shown for comparison (B). SP stimulated the release of $^{35}SO_4$ labeled macromolecules in a dose dependent fashion.

FIG. 2(A-B). Effects of fragments of substance P (SP) on sulfate flux from two segments from a ferret. Tissues were incubated in chambers with $^{35}SO_4$ on the luminal side, and after 3 h, fragments of SP were added to the submucosal sides of the chambers FIG. 2A: C-terminal fragment, SP 6-11 ($10^{-5}M$) stimulated secretion. FIG. 2B: N-terminal fragment. SP 1-9 ($10^{-5}M$) had no significant effect on secretion.

FIG. 3(A-B). Effect of proteinase inhibitors on substance P (SP)-induced change in sulfate flux from one tissue from a ferret. FIG. 3A: control tissue, incubated with $^{35}SO_4$ and exposed to SP ($10^{-6}M$). FIG. 3B: tissue pre-treated with the combination of 9 proteinase inhibitors described in the text (9 INHIB) potentiated the secretory response to SP ($10^{-6}M$).

FIG. 4. Effects of proteinase inhibitors on substance P (SP)-induced change in sulfate flux (mean±SE) from tissues from ferret tracheas. Open bars: response to SP ($10^{-6}M$) in control tissues from each group. Hatched bars: response to SP $10^{-6}M$ in tissues pre-treated with 9 proteinase inhibitors (9 INHIB; 10 μg/ml), phosphoramidon ($10^{-5}M$; PHOSP), thiorphan ($10^{-4}M$; THIOR), captopril ($10^{-4}M$; CAPTO), teprotide ($10^{-4}M$; TEPRO) or other inhibitors (OTHERS) including leupeptin, aprotonin, bacitracin, bovine serum albumin (each inhibitor, 10 μg/ml), or bestatin ($10^{-5}M$). *: $p<0.05$. Only phosphoramidon and thiorphan (enkephalinase inhibitors) potentiated the secretogogue effects of SP.

FIG. 5. Effects of increasing concentrations of the enkephalinase inhibitor thiorphan on substance P (SP)-induced sulfate flux from tracheal segments from 6 ferrets (mean±SE). Filled bars: increase in sulfate flux during the 15 min prior to adding drugs. Stippled bars: increase in sulfate flux after adding thiorphan in the concentrations indicated. Hatched bars: increase in sulfate flux induced by SP ($10^{-6}M$). *: $p<0.05$; compared to the spontaneous increase in sulfate flux; n=6 **: $p<0.05$; compared to the response to SP in control tissues; n=6. Thiorphan potentiated the SP-induced effects on secretion in a dose-dependent fashion.

FIG. 6. Effects of tachykinins and of the enkephalinase inhibitor, phosphoramidon, on release of $^{35}SO_4$-labeled macromolecules from ferret tracheas. Filled bar: Change in sulfate flux during a 15 min baseline period (BL) in the absence of drugs. Open bars: Responses to the tachykinins, substance P (SP), neurokinin A (NK-A), neurokinin B (NK-B), physalaemin (PHYS), eledoisin (ELED), and kassinin (KASS) (each drug, $10^{-5}M$). Hatched bars: Responses to tachykinins after pretreating tissues with phosphoramidon ($10^{-5}M$). *: $p<0.05$ compared to baseline **: $p<0.05$ compared to the response to the same tachykinins in the absence of phosphoramidon. Phosphoramidon potentiated the secretogogue effects of each tachykinin.

FIG. 7(A-B). Effects of trypsin on enkephalinase activity and substance P-induced mucus secretion in 3 ferrets. FIG. 7A: Enkephalinase activity in lung homogenates expressed as the degradation of ($^3$H-Tyr$^1$, DAla$^2$, Leu$^5$)enkephalin. FIG. 7B: Filled bar: change in mucus secretion during a 15 min baseline period in the absence of drugs. Open bar: Response to substance P (SP). Stippled bar: Change in mucus secretion after adding trypsin. Hatched bar: Change in mucus secretion induced by SP in tissues pretreated with trypsin. Data expressed as mean±SEM. Trypsin decreases enkephalinase activity and potentiates secretion induced by substance P.

FIG. 8. Effects of substance P (SP) and of the enkephalinase inhibitor leu-thiorphan on active tension in isolated segments of ferret tracheal smooth muscle. Results are reported as mean±SEM of 12 ferrets (SP$\leq 10^{-6}$M) or 6 ferrets (SP$\geq 5\times 10^{-6}$M). Significant differences from corresponding control values are indicated by: *=$p<0.05$; =$p<0.01$; *=$p<0.001$. Substance P alone (open squares) increased tension, but only at concentrations of $5\times 10^{-6}$M and higher. Leu-thiorphan (solid diamonds) caused a shift in the dose-response curve to lower concentrations of SP.

FIG. 9. Effects of receptor antagonists on active tension produced by substance P ($10^{-6}$M) in the presence of the enkephalinase inhibitor leu-thiorphan ($10^{-5}$M) in isolated segments of tracheal smooth muscle in ferrets. Each point is the mean±SE of the decreases in tension produced by each antagonist compared to the corresponding control responses to SP plus leu-thiorphan. Significant differences from control values are indicated by: *= $<0.05$; ***=$p<0.01$. The muscarinic antagonist, atropine ($10^{-5}$M), the SP antagonist, (DPro$^2$,DTrp$^{7,9}$)SP ($10^{-5}$M) and a combination of both drugs decreased SP plus leu-thiorphan-induced contractions significantly; the effect of the SP antagonist was greater than that of atropine.

FIG. 10. Effects of substance (SP) plus the enkephalinase inhibitor leu-thiorphan on active tension produced by electrical field stimulation (5 Hz) in isolated segments of tracheal smooth muscle in ferrets. Data are expressed as percent of control responses to electrical field stimulation without added drugs and are reported as mean ±SE (N=10 at=$10^{-5}$M; n=4 at $10^{-4}$M). Significant differences from SP alone or SP plus leu-thiorphan are indicated by: *=$p<0.05$; ***=$p<0.001$. Substance P alone augmented contractile responses to electrical field stimulation, and this augmentation was potentiated by leu-thiorphan.

FIG. 11. Effects of the enkephalinase inhibitor leu-thiorphan and of the substance P (SP) antagonist, (DPro$^2$,DTrp$^{7,9}$)SP on active tension produced by electrical field stimulation (5 Hz) in isolated segments of tracheal smooth muscle in ferrets. Data are expressed as percent of control responses to electrical field stimulation without added drugs and are reported as mean±SE (n=5). Significant differences from control values are indicated by: ***=$p<0.01$. Leu-thiorphan augmented contractions produced by electrical field stimulation, and this augmentation was inhibited by the SP antagonist ($10^{-5}$M).

FIG. 12. Effect of substance P (SP) (triangles), neurokinin A (NK-A) (circles) and neurokinin B (NK-B) (squares), and of the enkephalinase inhibitor, leu-thiorphan, on active tension in isolated segments of ferret tracheal smooth muscle. Data expressed as a percent of responses to acetylcholine ($10^{-3}$M). Results are reported as mean±SE of 10 ferrets ($10^{-6}$M) and 5 ferrets ($10^{-5}$M) Significant differences between contractions with and without leu-thiorphan ($10^{-5}$M) for each tachykinin were obtained. Leu-thiorphan (solid symbols) caused a shift in the dose-response curves to lower concentrations. Although NK-A was more potent than NK-B in the absence of leu-thiorphan, there were no significant differences in muscle contraction between NK-A and NK-B in the presence of leu-thiorphan ($10^{-5}$M).

FIG. 13. Effect of increasing concentrations of the enkephalinase inhibitor leu-thiorphan on active tension induced by substance P (SP), neurokinin A (NK-A), and neurokinin B (NK-B) in isolated segments of tracheal smooth muscle in ferrets. Data expressed as percent of responses to acetylcholine ($10^{-3}$M) and reported as mean±SE (n=5 at $10^{-5}$M; n=3 at $3\times 10^{-5}$M) Leu-thiorphan potentiated contractions induced by each tachykinin in a dose-dependent fashion.

FIG. 14. Effect of substance P (SP), neurokinin A (NK-A), and neurokinin B (NK-B) and of the tachykinin receptor antagonist, (DPro$^2$,DTrp$^{7,9}$)SP, on active tension produced by electrical field stimulation (5 Hz) in isolated segments of tracheal smooth muscle in ferrets. Data are expressed as percent of control responses to electrical field stimulation without added drugs. Each tachykinin potentiated electrically-induced contraction. SP had the most potent effect. The tachykinin receptor antagonist inhibited this potentiation.

FIG. 15. Effect of increasing concentrations of bradykinin FIG. 15A or lys-bradykinin (FIG. 15B) and of the enkephalinase inhibitor. leu-thiorphan ($10^{-5}$M) on active tension in isolated segments of ferret tracheal smooth muscle. Data are expressed as a percent of responses to acetylcholine ($10^{-3}$M). Results reported as mean±SE. Significant differences between contractions with and without leu-thiorphan are indicated by *=$p<0.05$. Bradykinin and lys-bradykinin increased active tension in a dose-dependent fashion. Leu-thiorphan caused a shift in both dose-response curves to lower concentrations.

FIG. 16. Effect of increasing concentrations of substance P and of the enkephalinase inhibitor leu-thiorphan ($10^{-5}$M), on active tension in isolated longitudinal segments of ileal smooth muscle in ferrets. Substance P alone (open circles) caused increased tension in a dose-dependent fashion. The enkephalinase inhibitor, leu-thiorphan (solid circles), potentiated the substance P-induced contractions.

FIG. 17(a)-(b). FIGS. 17(a) and 17(b) hereinafter referred to as FIG. 17. Amino acid sequence of rat enkephalinase.

FIG. 18(a)-(b). FIGS. 18(a) and 18(b) hereinafter referred to as FIG. 18. Amino acid sequence of human enkephalinase.

DETAILED DESCRIPTION

Enkephalinase preferentially hydrolyzes peptide bonds comprising the amino group of a hydrophobic residue, showing a marked preference for short peptides. The use of enkephalinase as a therapeutic agent for pathological conditions is established by the observations of the instant invention using as examples, the airway responses and effects on capillary permeability resulting from release of endogenous peptides, such as substance P or bradykinin. Enkephalinase, also known as neutral endopeptidase or kidney brush border neutral proteinase (E.C. 3.4.24.11, recommended name of the Enzyme Commission), and derivatives thereof may be used as a therapeutic agent in the treatment of those various pathological conditions. The experiments are described in detail below.

Endogenous peptides such as enkephalins, angiotensin I and angiotensin II, cholecystokinin, tachykinins e.g. substance P, neurokinin A or B, physalaemin, eledoisin, kassinin, kinins, e.g. bradykinin, lys-bradykinin (kallidin), other peptides, such as neurotensin, oxytocin, somatostatin, bombesin and chemotactic factors, for example eosinophil chemotactic factors, have been implicated in various physiological and pathological conditions. Examples of effects are cutaneous flushes, telangiectasia, diarrhea and bronchoconstriction resulting from the release of various peptides such as, substance P, bradykinin and bombesin from carcinoid tumors.

Circulating angiotensin I is converted by angiotensin-converting enzyme (ACE) to angiotensin-II, a potent vasoconstrictor. Systemic hypertension may arise from the effects of angiotensin II. Current therapy for systemic hypertension includes prevention of the conversion of angiotensin I to angiotensin II by inhibiting ACE. Cough is a side effect of this treatment with ACE inhibitors and is proposed to be due to the inhibition of breakdown of cough-provoking peptides (e.g., bradykinin). Enkephalinase degrades angiotensin I and II and thus may serve as an antihypertensive agent. Enkephalinase, by cleaving cough-provoking peptides such as bradykinin should eliminate cough as a side effect of antihypertensive therapy. Another pathological condition is tachykinin-mediated mucus hypersecretion from submucosal glands of the trachea following irritation of the airway epithelium, for example, by an allergen. In addition to mucus secretion there is likely to occur: inflammation, increased capillary permeability, neutrophil chemotaxis, edema and bronchial smooth muscle contraction (bronchoconstriction). In the skin, elevated levels of tachykinins or kinins produce sequelae of symptoms broadly referred to as dermatitis, including pain, itching, redness and heat and blistering. Tachykinins released in the gastrointestinal and urinary systems have been implicated in secretion e.g. salivation from the parotid gland, smooth muscle contraction of the ileum and esophagus, effects on frequency of urination, stimulation of secretion of water and electrolytes from the jejunum and pancreatic exocrine secretion. Tachykinins also promote embryonic implantation.

The data set forth in this specification establish that enkephalinase within the airway degrades substance P and other endogenous peptides to inactive metabolites. This inactivation is a mechanism for mitigating the effects of endogenous peptides on mucus secretion and bronchoconstriction This is based on the observation that thiorphan and phosphoramidon, specific inhibitors of enkephalinase, potentiated the secretory and contractile responses to substance P and other peptides in a concentration-dependent fashion. The inhibitors of enkephalinase were shown to have no direct effect on mucus secretion or muscle contraction. The effects of the enkephalinase inhibitors and of exogenous tachykinins on mucus secretion were observed when administered to the submucosal surface of tracheal tissue. Inhibitors of other enzyme systems did not alter endogenous peptide-induced secretion. For example, angiotensin converting enzyme (ACE) is known to be present in the lung and to degrade substance P. However, specific inhibitors of ACE did not potentiate substance P-induced secretion or bronchoconstriction. Similarly, inhibitors of serine proteases, proteases which are secreted from various cells (including neutrophils and mast cells) did not potentiate substance P-mediated mucus secretion from tracheal tissue. Leu-thiorphan was also observed to potentiate substance P-induced smooth muscle contraction of ileal tissue, indicating that enkephalinase present in gastrointestinal (ileal) tissue inhibits substance P-induced effects. The enkephalinase inhibitor, leu-thiorphan, was also observed to inhibit bradykinin and kallidin (lys-bradykinin) induced smooth muscle contraction of respiratory tissue. This demonstrates that endogenous enkephalinase inactivates kinins, as well as tachykinins. Thus enkephalinase appears to have a role in modulating endogenous peptide mediated mucus secretion and/or smooth muscle contraction in the airway. Enkephalinase injected intravenously was shown to inhibit substance P-induced extravasation of dye in rats. This provides direct evidence that enkephalinase administered to the body can prevent peptide-induced effects. Administration of enkephalinase or derivatives thereof by aerosol would apply the therapeutic agent locally to the trachea.

As used herein, enkephalinase or enkephalinase derivatives refers to proteins which are enzymatically active or are immunologically cross-reactive with enzymatically active enkephalinase. Enzymatically functional enkephalinase is capable of cleaving the $Gly^3$-$Phe^4$ amide bond of $^3H$-($DAla^2$, $Leu^5$)enkephalin in an assay as described by Llorens et al. (1982).

Enkephalinase or enkephalinase derivatives may be prepared using previously described methods of purification, see e.g. Malfroy and Schwartz. J. Biol. Chem. 259: 14365–14370 (1984) or by recombinant means as described in copending U.S. patent application Ser. No. 06/946,566, now abandoned and Ser. No. 07/002,478, now U.S. Pat. No. 4,960,700.

Included within the scope of enkephalinase as that term is used herein are enkephalinase having native glycosylation and the amino acid sequences of rat and human enkephalinase as set forth in FIGS. 17 or 18, analogous enkephalinases from other animal species such as bovine, porcine and the like, deglycosylated or unglycosylated derivatives of such enkephalinases, amino acid sequence variants of enkephalinase and in vitro-generated covalent derivatives of enkephalinases. All of these forms of enkephalinase are enzymatically active.

Amino acid sequence variants of enkephalinase fall into one or more of three classes: substitutional, insertional or deletional variants. Amino acid sequence variants are characterized by the predetermined nature of the variation, a feature that sets them apart from naturally occurring allelic or interspecies variation of the enkephalinase amino acid sequence. The variants typically exhibit the same qualitative biological activity as the naturally-occurring analogue, although variants also are selected to modify the characteristics of enkephalinase as will be more fully described below.

Amino acid substitutions are typically of single residues; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final derivative.

Substitutional variants are those in which at least one residue in the FIG. 17 or 18 sequences has been removed and a different residue inserted in its place. Such substitutions generally are made in accordance with the following Table 1 when it is desired to finely modulate the characteristics of enkephalinase.

TABLE 1

| Original Residue | Exemplary Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in enkephalinase properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain. e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

A major class of substitutional or deletional variants are those involving the transmembrane and/or cytoplasmic regions of enkephalinase. The cytoplasmic domain of enkephalinase is the sequence of amino acid residues commencing at either of two methionine residues shown in FIG. 17 (Met$^{-8}$ or Met$^{-1}$) and continuing for approximately 21-24 additional residues. In the rat and human sequence the Pro-Lys-Pro-Lys-Lys-Lys domain is believed to serve as a stop transfer sequence; the conformational bends introduced by the prolyl residues and the electropositive character provided by the lysyl residues act together with the transmembrane region described below, to bar transfer of enkephalinase through the cell membrane.

The transmembrane region of enkephalinase is located in the rat sequence at about residues 21-44 (where Asp is +1 as shown in FIG. 17), and in the human sequence at the analogous location. This region is a highly hydrophobic domain that is the proper size to span the lipid bilayer of the cellular membrane. It is believed to function in concert with the cytoplasmic domain to anchor enkephalinase in the cell membrane.

Deletion or substitution of either or both of the cytoplasmic and transmembrane domains will reduce the lipid affinity of the protein and improve its water solubility so detergents will not be required to maintain enkephalinase in aqueous solution. Deletion of the cytoplasmic domain alone, while retaining the transmembrane sequence, will produce enkephalinase which would be solubilized with detergent but which offers therapeutic advantages. The cytoplasmic domain-deleted enkephalinase will be more likely to insert into membranes when administered as a therapeutic agent, thereby targeting its activity to the immediate extracellular milieu in which it is ordinarily active, and would improve its formulation in salve or liposomal compositions containing hydrophobic micelles. Preferably, the cytoplasmic or transmembrane domains are deleted, rather than substituted, to avoid the introduction of potentially immunogenic epitopes.

For use in the invention herein, enkephalinase derivatives thereof may be formulated into either an injectable or topical preparation. Parenteral formulations are known and are suitable for use in the invention, preferably for i.m. or i.v. administration. Intramuscular or i.v. therapeutic preparations may preferably include transmembrane and cytoplasmic-transmembrane deleted enkephalinase derivative. The formulations contain therapeutically effective amounts of enkephalinase or derivatives thereof, are either sterile liquid solutions, liquid suspensions or lyophilized versions and optionally contain stabilizers or excipients. Lyophilized compositions are reconstituted with suitable diluents (e.g.) water for injection, saline and the like at a level of about from 0.001 mg/kg to 25 mg/kg where the biological activity is 10 nanomoles/mg/min when assayed at 25° C. in 50 mM, pH 7.4 HEPES buffer containing 0.1% Tween 20 using ($^3$H-DAla$^2$, Leu$^5$) enkephalin as substrate. Typically, the lyophilized compositions containing enkephalinase will be administered in a range of from about 0.01 mg/kg to about 20 mg/kg of the treated animal. Preferably, the lyophilized compositions containing enkephalinase will be administered in a range of from about 0.1 mg/kg to about 10 mg/kg of the treated animal.

Enkephalinase is formulated into topical preparations for local therapy by including a therapeutically effective concentration of enkephalinase in a dermatological vehicle. Such topical preparations may preferably include the cytoplasmic domain deleted enkephalinase derivative. The amount of enkephalinase to be administered, and the enkephalinase concentration in the topical formulations, will depend upon the vehicle selected, the clinical condition of the patient, the enkephalinase used and the stability of enkephalinase in the formulation. Thus, the physician will necessarily employ the appropriate preparation containing the appropriate concentration of enkephalinase in the formulation, as well as the amount of formulation administered depending upon clinical experience with the patient in question or with similar patients. The concentration of enkephalinase for topical formulations is in the range of greater than about from 0.1 mg/ml to about 25 mg/ml. Typically, the concentration of enkephalinase for topical formulations is in the range of greater than about from 1 mg/ml to about 20 mg/ml. Solid dispersions of enkephalinase as well as solubilized preparations can be used. Thus, the precise concentration to be used in the vehicle will be subject to modest experimental manipulation in order to optimize the therapeutic response.

Greater than about 10 mg enkephalinase/100 grams of vehicle may be useful with 1% w/w hydrogel vehicles in the treatment of skin inflammation. Suitable vehicles, in addition to gels, are oil-in-water or water-in-oil emulsions using mineral oils, petrolatum and the like.

Enkephalinase optionally is administered topically by the use of a transdermal therapeutic system (Barry, 1983, *Dermatological Formulations*, p. 181 and literature cited therein). Preferred topical preparations would comprise enkephalinase including the cytoplasmic-transmembrane domains. Most preferred topical preparations would comprise enkephalinase lacking the cytoplasmic-domain. While such topical delivery systems have been designed largely for transdermal administration of low molecular weight drugs, by definition they are capable of percutaneous delivery. They may be readily adapted to administration of enkephalinase or derivatives thereof and associated therapeutic proteins by appropriate selection of the rate-controlling microporous membrane.

Topical preparations of enkephalinase either for systemic or local delivery may be employed and may contain excipients as described above for parenteral administration and other excipients used in a topical preparation such as cosolvents, surfactants, oils, humectants, emollients, preservatives, stabilizers and antioxidants. Any pharmacologically acceptable buffer may be used e.g. tris or phosphate buffers. The topical formulations may also optionally include one or more agents variously termed enhancers, surfactants, accelerants, adsorption promoters or penetration enhancers, such as an agent for enhancing percutaneous penetration of the enkephalinase or other agents. Such agents should desirably possess some or all of the following features as would be known to the ordinarily skilled artisan: be pharmacologically inert, non-promotive of body fluid or electrolyte loss, compatible with enkephalinase (non-inactivating), and capable of formulation into creams, gels or other topical delivery systems as desired.

Enkephalinase may also be administered by aerosol to achieve localized delivery to the lungs. This is accomplished by preparing an aqueous aerosol, liposomal preparation or solid particles containing enkephalinase or derivatives thereof. Ordinarily, an aqueous aerosol is made by formulating an aqueous solution or suspension of enkephalinase together with conventional pharmaceutically acceptable carriers and stabilizers. The carriers and stabilizers will vary depending upon the requirements for the particular enkephalinase, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. The formulations also can include mucolytic agents as well as bronchodilating agents. The formulations will be sterile. Aerosols generally will be prepared from isotonic solutions. The particles optionally include normal lung surfactants.

Aerosols may be formed of particles in aqueous or nonaqueous (e.g., fluorocarbon propellant) suspension. Such particles include, for example, intramolecular aggregates of enkephalinase or derivatives thereof or liposomal or microcapsular-entrapped enkephalinase or derivatives thereof. The aerosols should be free of lung irritants, i.e. substances which cause acute bronchoconstriction, coughing, pulmonary edema or tissue destruction. However, nonirritating absorption enhancing agents are suitable for use herein. Sonic nebulizers preferably are used in preparing aerosols. Sonic nebulizers minimize exposing the enkephalinase or derivatives thereof to shear, which can result in degradation of enkephalinase.

Enkephalinase may be administered systemically, rather than topically, by injection i.m., subcutaneously or into vascular spaces, particularly into the joints, e.g. intraarticular injection at a dosage of greater than about 1 μg/cc joint fluid/day. The dose will be dependent upon the properties of the enkephalinase employed, e.g. its activity and biological half-life, the concentration of enkephalinase in the formulation, the site and rate of dosage, the clinical tolerance of the patient involved, the pathological condition afflicting the patient and the like as is well within the skill of the physician.

The enkephalinase of the present invention may be administered in solution. Preferably, enkephalinase lacking the transmembrane domain or the cytoplasmic and transmembrane domains would be used for administration in solution. The pH of the solution should be in the range of pH 5 to 9.5. preferably pH 6.5 to 7.5. The enkephalinase or derivatives thereof should be in a solution having a suitable pharmaceutically acceptable buffer such as phosphate, tris (hydroxymethyl) aminomethane-HCl or citrate and the like. Buffer concentrations should be in the range of 1 to 100 mM. The solution of enkephalinase may also contain a salt, such as sodium chloride or potassium chloride in a concentration of 50 to 150 mM. An effective amount of a stabilizing agent such as an albumin, a globulin, a gelatin, a protamine or a salt of protamine may also be included and may be added to a solution containing enkephalinase or to the composition from which the solution is prepared.

Systemic administration of enkephalinase is made daily, generally by intramuscular injection, although intravascular infusion is acceptable. Administration may also be intranasal or by other nonparenteral routes. Enkephalinase may also be administered via microspheres, liposomes or other microparticulate delivery systems placed in certain tissues including blood. Topical preparations are applied daily directly to the skin or mucosa and then preferably occluded, i.e. protected by overlaying a bandage, polyolefin film or other barrier impermeable to the topical preparation.

The method is illustrated by way of the following examples, which are not to be construed as limiting the invention.

EXAMPLE 1

Measurement of Substance P

The content of substance P-like immunoreactivity in ferret trachea was determined by mincing the trachea in 10 times the tissue weight of 2N acetic acid, extracting overnight, centrifuging the tissue fragments, and applying the supernatant to a C-18 column (Sep-Pak; Waters and Associates) that had been equilibrated with water containing 0.1% trifluoroacetic acid (TFA) and precycled with 0.2 ml of 0.5 μg/ml poly-L-Lysine (Sigma) in 0.1% TFA. The Sep-Pak was then washed sequentially with a step gradient consisting of 4.0 ml each of 0, 20, 40 and 60% methanol in 0.1% TFA in water, with the substance P eluting at 60% methanol. The methanol was evaporated under $N_2$, and the samples were then lyophilized and reconstituted in assay buffer before being assayed. The assay buffer consisted of 0.5% 2-mercaptoethanol, 0.25% bovine serum albumin (BSA), 0.03% NaN₃ in 0.05M NaPO₄ buffer at a pH of 7.4. Samples of medium obtained directly from Ussing chambers and the tissue extracts were assayed using a pre-equilibration radioimmunoassay. Separation of free radiolabeled substance P from antibody-bound radiolabeled substance P was achieved using Dextran T70-coated charcoal (Pharmacia).

Radiolabeled substance P was made by coupling substance P to Bolton-Hunter reagent (Bolton, A. E. and Hunter, W. M., Biochem. J. 133: 529-539 [1973]) and then purifying the coupled product using HPLC (Hewlett Packard model 1090). The reaction mixture was applied to a 10 $\mu$m C-18 reverse phase HPLC column (Waters and Associates) and was eluted isocratically from the column at a flow rate of 1 ml/min using 55% methanol and 0.045% TFA in water. The mono-derivatized substance P was radioiodinated using chloramine-T (McConahey, P. and Dixon, R., Methods in Enzymology 70: 210-213 [1980]). The reaction mixture was applied to a Sep-Pak C-18 column, and the iodinated Bolton-Hunter derivative of substance P was eluted with 60% methanol.

Rabbits were immunized with a mixture of Freund's complete adjuvant, buffered saline and substance P that had been coupled to purified BSA using glutaraldehyde. Substance P was conjugated by dissolving 25 mg monomeric BSA and 5 mg substance P in 1.0 mL of 0.1M NaPO₄ buffer at a pH of 6.8, and then, with constant stirring, slowly added 0.1 mL of 0.5% glutaraldehyde in NaPO₄ buffer. The mixture was incubated for at least 2 hours, after which time, the reaction was quenched by adding 1.0 mL of 0.1 M $(NH_3)_2CO_3$. After stirring for an additional 30 minutes, the mixture was exhaustively dialyzed against distilled $H_2O$, lyophilized, and weighed.

Serum was harvested, lyophilized, and frozen. Serum was reconstituted in distilled water for radioimmunoassays. The substance P antiserum was tested for cross reactivity against other peptides including bradykinin, lysyl-bradykinin, vasoactive intestinal peptide, somatostatin, cholecystokinin-8, gastrin, bombesin and neurotensin (Peninsula Labs, Belmont, Calif.). Additionally, we tested several proteinase inhibitors (see below), the N-terminal fragment of substance P, substance $P_{1-9}$, and the C-terminal fragment, substance $P_{6-11}$ (Peninsula Labs).

Ferret tracheal segments contained an average of 0.58±0.230 pmoles of substance P-like immunoreactivity per gm. wet weight (n=3), suggesting that substance P is present in the airways of ferrets.

EXAMPLE 2

Mucus Secretion from Lung Tissue

Mucus secretion from tracheal segments of 36 ferrets was measured using methods described earlier (Borson, D. B. et al., J. Appl. Physiol. 57: 457-466 [1984]). Briefly after anesthetizing adult male ferrets weighing 1-2 kg with sodium pentobarbital (45-60 mg/kg, ip), the trachea was removed and washed in medium 199/Earles $HCO_3$ bubbled with 95% $O_2$ - 5% $CO_2$ at 38° C. Tracheal segments were mounted in plastic Ussing-type chambers connected to perfusion chambers made of siliconized glass (MRA Inc., Clearwater, Fla.). After exposing both sides to medium 199, 0.167 mCi $Na_2$-³⁵$SO_4$ was added to the submucosal side. At 15 minute intervals, the medium was drained from the luminal side and replaced with fresh unlabeled medium. Each sample was placed in dialysis tubing (Spectropore no. D1615-1; MW cutoff: 12-14,000) and exhaustively dialyzed with the rest of the samples from that experiment against at least 6 changes of distilled water (4 liters each) containing excess unlabeled $SO_4$ and sodium azide (10 mg/L) to prevent bacterial degradation of the macromolecules. After dialysis, the bound radioactivity of each sample was determined using a Beckman Instruments beta counter (model LS 7500). Molecular weight profiles of the materials secreted were determined by first desalting samples using a Sephadex G-50 column, then concentrating carbohydrate-containing molecules on DEAE Sephacel, and determining apparent molecular size under denaturing conditions (4M guanidine, 10 mM 2-mercaptoethanol, 0.1% Triton X-100) using a Sepharose CL-6B column Previous studies demonstrated that analysis of samples using dialysis and column chromatography yielded quantitatively similar results (Borson et al., J. Appl. Physiol. 57:457-466 [1984]).

Characteristics of the response to substance P including the time course, concentration dependence, and reproducibility were studied. Tracheal segments from 8 ferrets were incubated in the presence of radiolabel for 3 hours to which were added different concentrations of substance P ($10^{-9}M$ to $10^{-5}M$; Peninsula Labs, Belmont, Calif.). Reproducibility of the response to substance P was established by adding $10^{-6}M$ substance P twice, first after 3 hours, and again after 4 hours of incubation. All treatments were randomized with regard to the site of sampling in the trachea to eliminate systematic bias.

After mounting tissues in the chambers and adding radiolabel, the rate of secretion of ³⁵$SO_4$-macromolecules into the luminal side of the tissues increased, and by two to three hours, secretion was increasing in an approximately linear fashion. After three hours of labeling, tissues secreted at an average rate of 111.8±15.6 pmol bound $SO_4/cm^2/h$. At this time, the average increase in flux of bound $SO_4$ per sample interval was 11.7±2.5 pmol bound $SO_4/cm^2/h$ (10.5% of baseline). When added to the submucosal sides of tissues, substance P increased secretion within 15 min, after which time, secretion returned towards baseline, and finally reached the values obtained by extending the pre-stimulus baseline forward in time. Gel permeation chromatography indicated that 85% of the radiolabeled materials secreted in response to substance P had molecular weights in excess of $10^6$, suggesting that most were likely to be mucins or proteoglycans. Substance P increased flux of bound $SO_4$ in a concentration-dependent fashion, with a threshold of $10^{-9}M$ and a response to $10^{-5}M$ substance P of 156.4±26.1 pmol bound $SO_4/cm^2/h$ or 155±42% above the pre-stimulus baseline (FIG. 1). The substance P-induced secretion was significantly greater than the increase due to time alone for all concentrations of substance P greater than $10^{-9}M$ ($p<0.05$; n=6 each). Furthermore, repeated stimulation caused repeated responses. The second response was an average of 71.4±24.2% of the first response ($p<0.1$; n=4). Removing the substance P from the medium after the first stimulus increased the magnitude of the second response slightly to 91.1±48.3% of the first response, but this was not significantly different from the second response of the tissues that were continuously exposed to substance P ($p<0.2$; n=4 ea).

The C-terminal fragment, substance $P_{6-11}$ ($10^{-5}M$) caused a potent release of bound $SO_4$, whereas the N- terminal fragment, substance $P_{1-9}$, did not (369.4±18.3 vs 33.7±24.7 pmol bound $SO_4/cm^2/h$; p<0.05; n=4 ea) (e.g., FIG. 2). The response to substance $P_{6-11}$ was significantly greater than the response to substance $P_{1-11}$ at the same concentration (156.4±26.1 pmol bound $SO_4/cm^2/h$; p<0.001; n=4). Secretion induced by substance $P_{1-9}$ was not different from the spontaneous change in baseline flux in these tissues due to time alone (−18.4±16.8 pmol bound $SO_4/cm^2/h$; p>0.1; n=4).

EXAMPLE 3

Effect of Proteinase Inhibitors on Substance P-Induced Mucus Secretion

In the next series of experiments, the effects of substance P metabolism on secretory responses to substance P was studied. Different enzymes cleave substance P at different sites. The active portion of the peptide, the C-terminal fragment causes secretory activity. Enkephalinase was shown to cleave substance P to the inactive fragment substance $P_{1-9}$.

The effects of endogenous proteinases were studied by incubating at least two tissues from each of 4 ferrets for 30 minutes in medium for 2.5 hours and adding a combination of nine (9) proteinase inhibitors to the submucosal side of each tissue (10 μg/mL each). The inhibitors used included leupeptin, antipain, pepstatin A, thiorphan, substance $P_{1-9}$ (Growcott, J. W. and Tarpey, A. V. Eur. J. Pharm 84: 107–109 [1982]) and the angiotensin converting enzyme inhibitor, teprotide (Peninsula Labs), aprotonin, BSA, and bacitracin (Sigma). Thirty minutes after addition of inhibitor, substance P ($10^{-6}M$) was added to the submucosal side. In the absence of proteinase inhibitors, this concentration of substance P caused consistent and submaximal effects. In some of the tissues, the combination of inhibitors stimulated secretion, and when present, the effect reached a maximum within 30 min after adding the inhibitors. The mean responses to substance P in the presence of inhibitors was compared with the mean responses of two control segments from each of the same animals. Subsequent experiments tested the effects of the individual proteinase inhibitors, thiorphan, teprotide, phosphoramidon (Sigma), captopril (Squibb Pharmaceuticals, Inc.), teprotide, bovine serum, albumin, bacitracin, leupeptin, aprotonin, and bestatin (Sigma), an inhibitor of an aminopeptidase in brain that degrades enkephalins (Chaillet, P. et al., Eur. J. Pharmacol. 86: 329–336 [1983]).

The concentration-dependence of enkephalinase inhibition was explored by adding thiorphan in different concentrations to different tissues. To determine whether the secretory effect of substance P might be mediated indirectly via the release of endogenous enkephalins, we tested the effects of met-enkephalin (Peninsula Labs) on secretory responses.

We calculated the flux of bound $SO_4$ ($^JSO_4$) from the cpm in the dialyzed samples according to the equation modified from (Corrales, R. J. et al , J. Appl. Physiol. 56: 1076–1082 [1985]):

$$J_{SO_4}(pmol\ SO_4/cm^2/h) = \frac{(cpm\ recovered/15\ min \times 4) \times (811 \times 10^6\ pmol\ cold\ SO_4/5\ mL)}{0.5\ cm^2 \times cpm\ in\ 5.0\ mL\ of\ hot\mbox{-}side\ medium}$$

Changes in flux due to drugs were calculated by subtracting the flux during the 15 min period prior to adding drugs from the flux observed for that tissue either 15 or 30 min after adding drugs, which ever was higher. Mean fluxes or changes in fluxes for each condition were compared with each other by one-way analysis of variance. Newman-Keuls test for multiple comparisons was used to determine differences between groups (Zar, J. H., "Multiple Comparisons" in *Biostatistical Analysis* [Prentice Hall, Englewood Cliffs, N.J. 1974]).

When added to the submucosal sides of the tissues, the combination of 9 proteinase inhibitors increased the flux of bound $SO_4$ into the lumen slightly, but not significantly (45.8±28.2 pmol bound $SO_4/cm^2/h$) compared to the increase due to time alone (12.3±6.2 pmol bound $SO_4/cm^2/h$). After adding substance P to the submucosal sides of these tissues, the flux of bound $SO_4$ increased by an average of 383.5±148 pmol bound $SO_4/cm^2/h$, or 438.6±105.2% of the response to substance P of the control tissues from the same animals (83.7±21.4 pmol bound $SO_4/cm^2/h$, p<0.05; n=4) (FIGS. 3 and 4). The increased response to substance P was not due to additive effects of the inhibitors and substance P because the sum of the individual effects, 83.7 pmol bound $SO_4/cm^2/h$ (substance P) plus 45.8 pmol bound $SO_4/cm^2/h$ (inhibitors) was 129.5 pmol bound $SO_4/cm^2/h$, or only 34% of the response to substance P in the presence of the inhibitors (383.5 pmol bound $SO_4/cm^2/h$).

Of the individual inhibitors studied, only thiorphan and phosphoramidon, inhibitors of enkephalinase, potentiated substance P-induced secretion (FIGS. 4 and 5). When added to the submucosal side of the tissues at $10^{-4}M$, thiorphan by itself increased the flux of bound $SO_4$ into the lumen by an average of 57±17.8 pmol bound $SO_4/cm^2/h$. This was significantly greater than the spontaneous increase in flux in the same tissues before adding thiorphan (20.5±6.3 pmol bound $SO_4/cm^2/h$; p<0.05; n=6). At lower concentrations, thiorphan did not stimulate secretion significantly. However, thiorphan potentiated the secretory response to substance P in a concentration-dependent fashion, with a threshold of approximately $10^{-8}M$ (FIG. 5). In tissues pretreated with thiorphan ($10^{-4}M$), substance P increased flux of bound $SO_4$ by an average of 268.0±58.0 pmol/$cm^2$/h (502±147% of control; p<0.05; n=6). This average response was significantly greater than that of control tissues from the same animals (79.2±13.0 pmol bound $SO_4/cm^2/h$; p<0.05; n=6). The increase in substance P-induced secretion was not an additive effect of thiorphan and substance P: the sum of the individual effects, 79.2 pmol bound $SO_4/cm^2/h$ (substance P) plus 57.0 pmol bound $SO_4/cm^2/h$ (thiorphan), or 136.2 pmol bound $SO_4/cm^2/h$, was only 51% of the response to substance P in the presence of thiorphan (268.0 pmol bound $SO_4/cm^2/h$). In tissues treated with phosphoramidon ($10^{-5}M$), substance P ($10^{-6}M$) increased flux by an average of 357±91.9 Pmol bound $SO_4/cm^2/h$, which was significantly greater than the responses of the control tissues from the same animals (62.3±24.8 pmol bound $SO_4/cm^2/h$; p<0.05; n=4 ea).

In contrast to inhibitors of enkephalinase, inhibitors of other proteinases did not potentiate substance P-induced secretion (FIG. 4). Thus, captopril and teprotide, inhibitors of kininase II (angiotensin converting enzyme), potentiated substance P-induced secretion slightly (by 44±27%, and 49±39%, respectively), but the increases were not significantly different from responses of the control tissues from the same animals (p>0.2; n=4 ea). Similarly, leupeptin, aprotonin, bacitracin, BSA. and bestatin failed to potentiate substance P-induced secretion.

Experiments were carried out to investigate whether the secretory response to substance P might be mediated by endogenously-released enkephalins. Met-enkephalin did not stimulate secretion significantly. After adding met-enkephalin ($10^{-4}$M) the change in flux of bound $SO_4$ was $6.7 \pm 4.2$ pmol/cm$^2$/h, which was not different from the change in flux in control tissues at the equivalent time of $7.0 \pm 1.5$ pmol bound $SO_4$/cm$^2$/h (p<0.5; n=4). These studies indicate that enkephalinase present in airway tissue inhibits substance P-induced secretion.

EXAMPLE 4

Effects of Enkephalinase Inhibitors on Secretory Responses to Tachykinins

In this next series of experiments, the effects of different tachykinins and the enkephalinase inhibitor, phosphoramidon were compared. Tissues from ferret tracheas were mounted in chambers and labeled using previously described methods (Example 2). Tissues were then exposed to one of the tachykinins substance P (SP), neurokinin A (NK-A), neurokinin B (NK-B), eledoisin (ELED), physalaemin (PHYS), or kassinin (KASS). Each tachykinin was administered at $10^{-5}$M in the absence or presence of phosphoramidon ($10^{-5}$M, 30 min; Sigma). The release of high molecular weight $^{35}SO_4$ was determined as described above in Example 2. The data is shown in FIG. 6. In the absence of phosphoramidon, most of the tachykinins stimulated secretion with an order of potency;

substance
P > physalaemin = eledoisin = kassinin > neurokinin A.

(p<0.05, n=5 each). Neurokinin B, in the absence of phosphoramidon, was ineffective. However, in tissues pretreated with phosphoramidon, secretory responses to each tachykinin were significantly increased (P<0.05, n=5 each). Furthermore, in the presence of phosphoramidon, the order of potency was altered:

Substance P = neurokinin
A = physalaemin = eledoisin = kassinin > neurokinin B.

In the absence of enkephalinase inhibition, the effect of substance P was greater than that of neurokinin A. After enkephalinase inhibition, the effects of substance P and neurokinin A were the same. These results suggest that enkephalinase cleaves neurokinin A with greater efficiency than it cleaves substance P. They also indicate that enkephalinase present in airway tissue inhibits secretion induced by various tachykinins.

EXAMPLE 5

Localization and Functional Properties of Enkephalinase in Airways

In this series of experiments, the tissue locations of enkephalinase were determined. Enkephalinase was purified from the ferret kidney to near homogeneity using published methods (Malfroy and Schwartz, Supra). Enkephalinase activity in membrane fractions derived from the vagus nerve, tracheal epithelium, submucosa, muscle, lungs, and kidneys of ferrets was determined. Ferrets were anesthetized, and the vagi, trachea, lungs, and kidneys removed. The tracheal epithelium, submucosa, and muscle were separated from each other by incubating the trachea in $Ca^{++}$-free medium for 15 minutes, after which time, the epithelium was easily removed. The muscle was then separated from the gland-containing submucosa. Each tissue was minced and then homogenized in 50 mM HEPES buffer (pH 7.4) using a Polytron homogenizer.

Enkephalinase activity was measured by determining the rates of cleavage of ($^3$H-Tyr$^1$, DAla$^2$, Leu$^5$)enkephalin (Research Products International) by membrane fractions or purified enkephalinase. Fifty $\mu$l of membrane fraction was incubated for 40 minutes at room temperature with 50 $\mu$l of buffer containing ($^3$H-Tyr$^1$, DAla$^2$, Leu$^5$)enkephalin (20 nM), after which time the reaction was quenched by adding 50 $\mu$l of 2N HCl.

Seventy-five $\mu$l of this solution was applied to columns containing polystyrene beads (Poropak-Q); the characteristic metabolite, $^3$H-Tyr-DAla-Gly, eluted with water, and the radioactivity determined. The protein concentrations were determined by the Bradford procedure (Bradford, M. M. Analytical Biochem. 72:248–254 [1976]), and results of enkephalinase activities were expressed as fmoles substrate cleaved per min per mg protein. Results are shown in Table 2.

TABLE 2

Localization of Airway Enkephalinase And Interactions with Leu-Thiorphan and Substrates

| | Tissues | | | | | |
|---|---|---|---|---|---|---|
| | mucosa | Muscle | Lung | Kidney | Epthe-Vagus/N. | Sublium |
| Enkephalinase Activity** | 1226 ±211 | 520 ±155 | 540 ±70 | 7419* | 614 ±116 | 690 ±187 |
| $K_I$ | | | | | | |
| leu-thiorphan (nM) | 2.1 | 8.7 | 2.8 | 2.1 | 2.8 | 3.3 |
| (DAla$^2$, Leu$^5$)-enkephalin ($\mu$M) | 53.2 | 20.0 | 30.6 | 32.4 | 24.1 | 52.0 |
| Substance P ($\mu$M) | 5.4 | 5.3 | 3.2 | 3.6 | 2.7 | 4.1 |
| Neurokinin A ($\mu$M) | 6.9 | 9.7 | 4.4 | 5.2 | 3.0 | 6.1 |

*Mean of triplicate determination from one experiment.
**Data expressed as fmoles/min/mg protein.

Each tissue cleaved the substrate, with the highest activity in the airway present in the submucosa. Leucine-thiorphan (leu-thiorphan, an enkephalinase inhibitor) inhibited substrate cleavage with affinity constants ($K_I$) in the nanomolar range for each tissue. In contrast with leu-thiorphan, other proteinase or peptidase inhibitors ($10^{-5}$M), did not inhibit substrate cleavage by any tissue. These inhibitors included: captopril, an inhibitor of angiotensin converting enzyme; bestatin, an inhibitor of aminopeptidases; aprotonin, an inhibitor of serine proteinases; or, leupeptin, an inhibitor of serine or thiol proteinases. Therefore, substrate cleavage is due exclusively to the action of enkephalinase. The peptides, (DAla$^2$,Leu$^5$)enkephalin, substance P, and neurokinin A also inhibited substrate cleavage with affinity constants ($K_I$) that, for each substrate, were the same for all tissues (see Table 2). The affinity of enkephalinase for substance P and for neurokinin A is approximately ten times the affinity of enkephalinase for (DAla$^2$,Leu$^5$)enkephalin. Because the affinity constants for substance P and for neurokinin A are the same, the differences in activities of these peptides on mucus secretion (Example 4) and muscle contraction (Example 8) are probably due to differences in turnover numbers (Kcat) and not to differences in affinities of enkephalinase for the substrates.

EXAMPLE 6

Effect of Trypsin on Enkephalinase Activity and Substance P-induced Mucus Secretion In this series of experiments, the effects of a prototype extracellular proteinase on enkephalinase and substance P-mediated mucus secretion were studied. The rationale for these studies is that a variety of proteinases are released from different cells and tissues (e.g. neutrophil elastase, alkaline proteinase, mast cell tryptase and chymase), and if these proteinases destroy enkephalinase, then alterations in peptide-induced secretion should be observed. This hypothesis was tested using trypsin ($10^{-11}$ to $10^{-5}$M; 15 min) a prototype serine proteinase. The effect of trypsin on enkephalinase activity of lung homogenates measured as degradation of ($^3$H-Tyr-DAla$^2$-Leu)enkephalin, and mucus secretion from tracheas of 3 ferrets was determined.

Trypsin incubation (15 minutes) decreased enkephalinase activity in homogenates of lungs (FIG. 7) in a concentration-dependent fashion, with a threshold above $10^{-11}$M and a maximal effect at $10^{-5}$M. Additionally, trypsin ($10^{-5}$M, 30 min) by itself did not increase mucus secretion more than the increase due to time alone. However, trypsin increased the secretory response to substance P. Thus, as is the case for enkephalinase inhibitors (e.g. thiorphan), the decrease in enkephalinase activity caused by trypsin is associated with increased secretory responses to substance P. Therefore, it is likely that other proteinases (e.g. those from inflammatory cells, mast cells, neutrophils, etc.) also might alter peptide-induced responses indirectly, by regulating the amount or activity of enkephalinase in the tissue.

EXAMPLE 7

Effect of Proteinase Inhibitors on Substance P-Induced Airway Smooth Muscle Contraction Twenty-seven ferrets were anesthetized with pentobarbital sodium (45-60 mg/kg, i.p.), and the trachea were removed. Transverse rings (8 mm long) were cut from the trachea and mounted in glass chambers filled with 14 ml of Krebs-Henseleit solution of the following composition (in mMoles/L): NaCl 118, KCl 5.9, CaCl$_2$ 2 2.5, MgSO$_4$ 1.2, NaH$_2$PO$_4$ 1.2, NaHCO$_3$ 25.5, glucose 5.6, 0.1% bovine serum albumin, and penicillin-streptomycin (100 Units/ml). The solution was maintained at 37° C. and was aerated continuously in a mixture of 95% O$_2$-5% CO$_2$, which produced a pH of 7.4. Six tracheal rings were studied concurrently.

The tracheal rings were connected to strain gauges (Grass FT03) for continuous recording of isometric tension, and the rings were placed between two rectangular platinum electrodes (6×40 mm) for electrical field stimulation. The rings were initially stretched to a tension of 20 g for 30 seconds and were then allowed to equilibrate for 1 hour while resting tension was adjusted to 4 g (Skoogh, B-E. et al., J. Appl. Physiol. 53: 253-257 [1982]). During equilibration, the medium was changed every 15 minutes. Preliminary studies showed that maximal responses to electrical field stimulation (biphasic, pulse duration 0.5 ms; 20 V for 20 s, frequency, 20 Hz) were obtained with 4 g of resting tension. Id.

The responsiveness to substance P (using concentrations ranging from $10^{-8}$M to $10^{-5}$M) and to leu-thiorphan and cumulative dose-response curves to substance P (Peninsula Labs) were obtained. Each succeeding concentration of substance P was added after contraction reached a plateau. After completion of the first dose-response curve to substance P, leu-thiorphan ($10^{-5}$M, Squibb Pharmaceutical) was added to the organ bath. Following a 15 minute incubation, a second dose-response curve to substance P was obtained.

The N-terminal fragment, substance P$_{1-9}$ was studied because enkephalinase cleaves substance P between the 9 and 10 positions (Matsas, R. et al., Proc. Natl. Acad. Sci. [USA] 80: 3111-3115 [1983]). generating that fragment. ($10^{-5}$M Peninsula Labs). Experiments were also carried out with (DPro$^2$, DTrp$^{7,9}$)-substance P ($10^{-5}$M) (Peninsula Labs), a substance P antagonist (Hakanson, R. et al., Br. J. Pharmac. 77: 697-700 [1982]) by adding the antagonist after the response to substance P ($10^{-6}$M) and leu-thiorphan ($10^{-5}$M) reached a plateau.

Substance P was dissolved in 0.1M acetic acid, and leu-thiorphan was dissolved in 1% ethanol to give stock solutions of approximately $10^{-3}$M. These drugs were stored at −25° C., and aliquots were thawed and diluted in Krebs-Henseleit solution for each experiment.

Data were expressed as mean±SE. For the dose-response curves to substance P, the means between two groups at each concentration were compared by a paired t test. For the studies of electrical field stimulation, responses were compared by one way analysis of variance and Newman-Keuls multiple range test. Significance was accepted at $P<0.05$.

Substance P alone caused an increased muscle tension, but only at concentrations of $5 \times 10^{-6}$M or greater (FIG. 8). Addition of leu-thiorphan ($10^{-5}$M) alone had no significant effect on resting tension, but it shifted the dose-response relationship to substance P to lower concentrations by approximately one log unit (FIG. 8). In contrast to substance P, the N-terminal fragment substance P$_{1-9}$ ($10^{-5}$M), had no significant effect on resting tension (n=3).

The contraction produced by substance P ($10^{-6}$M) in the presence of leu-thiorphan was decreased by the substance P antagonist (DPro$^2$, DTrp$^{7,9}$)substance P ($10^{-5}$M) (36.0±10.0% of control). The substance P antagonist decreased substance P-induced contractions significantly more than did atropine alone (p<0.01) (FIG. 9).

Electrical field stimulation-induced contraction in the presence of substance P ($5 \times 10^{-11}$M) and either captopril (Squibb Pharmaceutical) ($10^{-5}$M), bestatin (Sigma) ($10^{-5}$M) or leupeptin (Peninsula Labs) ($10^{-5}$M) was measured to determine whether inhibition of angiotensin converting enzyme (ACE), aminopeptidases, and serine or thiol proteinases were responsible for potentiating responses to electrical field stimulation. Increasing concentrations of leu-thiorphan ($10^{-11}$ to $10^{-4}$M) were added and the stimuli repeated to determine whether leu-thiorphan modulated electrical field stimulation-induced contractions. The effects of leu-thiorphan on electrically induced contraction was studied using five additional ferrets. After determining control responses to electrical field stimulation (5 Hz), leu-thiorphan ($10^{-5}$M; 15 min) was added, the stimulus repeated, (DPro$^2$,DTrp$^{7,9}$)substance P, the substance P antagonist (10$^{-5}$M; 15 min; Peninsula Labs) was added, and the stimulus was repeated.

Substance P alone, even in very low concentrations (5×10$^{-11}$M), augmented the responses to electrical field stimulation (FIG. 10). Substance P (10$^{-11}$ or 10$^{-10}$M), reproducibly augmented electrical field stimulation-induced contraction, with no significant tachyphylaxis of the effect, even after 5 responses (n=3). Leu-thiorphan at concentrations up to 10$^{-4}$M did not alter resting tension in any experiment. However, addition of increasing concentrations of leu-thiorphan produced dose-related increases in the responses to electrical field stimulation, with a threshold of approximately 10$^{-9}$M and a maximum effect at 10$^{-5}$M (FIG. 10).

Leu-thiorphan potentiated the response to electrical field stimulation in a concentration-dependent fashion (FIG. 11). (DPro$^2$,DTrp$^{7,9}$)substance P (10$^{-5}$M) significantly inhibited the increase in the response to electrical field stimulation induced by leu-thiorphan (101.6±1.7% compared to 118±1.7% in the presence of leu-thiorphan; p<0.01; n=5).

In contrast to the effects of leu-thiorphan, none of the other peptidase inhibitors used potentiated the response to electrical field stimulation in the presence of substance P (5×10$^{-11}$M) (p<0.5; n=3).

These studies establish that enkephalinase is present in airway muscle and nerves, and that it decreases substance P-induced effects, including bronchoconstriction and potentiation of neurotransmission to airway smooth muscle.

Enkephalinase is involved in decreasing substance P-induced effects because leu-thiorphan augmented substance P-induced effects, whereas other proteinase and peptidase inhibitors such as captopril, an inhibitor of angiotensin converting enzyme (Turner. A. J. et al., Biochem. Pharmacol. 34: 1347–1356 [1985]), bestatin, an inhibitor of aminopeptidases, or leupeptin, an inhibitor of serine or thiol proteinases, were without effect.

EXAMPLE 8

Effect of Proteinase Inhibitors on Tachykinin Induced Contraction of Airway Smooth Muscle The methods used to excise tracheal tissue, mount and electrically stimulate the tissue were identical to those described above. The responses to tachykinins and to leu-thiorphan, cumulative dose-response curves to substance P (Peninsula Labs), neurokinin A (Peninsula Labs) and neurokinin B (Peninsula Labs) were obtained using concentrations ranging from 10$^{-11}$M to 10$^{-5}$M in the presence and absence of leu-thiorphan (10$^{-5}$M, 15 min; Squibb Pharmaceutical). Each succeeding concentration of tachykinin was added after the previous contraction had reached a plateau.

Electrical field stimulation-induced contractions were measured in the presence of substance P (10$^{-10}$M), neurokinin A (10$^{-10}$M) and neurokinin B (10$^{-10}$M), combined with either captopril (10$^{-5}$M; 15 min; Squibb Pharmaceutical), bestatin (10$^{-5}$M); 15 min; Sigma) or leupeptin (10$^{-5}$M; 15 min; Peninsula Labs) to determine whether inhibition of angiotensin converting enzyme (ACE), aminopeptidases, or serine or thiol proteinases were responsible for potentiating responses to electrical field stimulation.

Data were expressed as mean±SE. For the dose-response curves to tachykinins the means between two groups at each concentration were analyzed by an unpaired t test. For the study of electrical field stimulation, responses were compared by one way analysis of variance and Newman-Keuls multiple range test. Significance was accepted at p<0.05.

Substance P, neurokinin A and neurokinin B alone caused smooth muscle contraction, but only at concentrations of 10$^{-6}$M or greater for neurokinin A and 10$^{-5}$M for substance P and neurokinin B (FIG. 12). Contractions induced by tachykinins were compared at 10$^{-6}$M and 10$^{-5}$M, indicating a rank order of potency:

neurokinin A > substance P > neurokinin B, although statistically significant differences were obtained only between neurokinin A and substance P (p<0.05) or neurokinin A and neurokinin B (p<0.01) at 10$^{-6}$M, and between neurokinin A and neurokinin B (p<0.01) at 10$^{-5}$M. Addition of leu-thiorphan (10$^{-5}$M) alone had no significant effect on resting tension, but shifted the dose-response curves to substance P, neurokinin A and neurokinin B to lower concentrations by approximately one-log unit for substance P, two-log units for neurokinin A, and three-log units for neurokinin B (FIG. 12). A rank order of potency of tachykinins in the presence of leu-thiorphan was:

neurokinin A = neurokinin B > substance P.

Leu-thiorphan potentiated the responses to tachykinins in a concentration-dependent fashion, with a threshold of approximately 10$^{-7}$M and a maximum effect at 10$^{-5}$M (FIG. 13). In contrast to the effects of leu-thiorphan, none of the other peptidase inhibitors used potentiated the response to electrical field stimulation in the presence of substance P, neurokinin A or neurokinin B (10$^{-7}$M).

Substance P, neurokinin A and neurokinin B each potentiated the responses to electrical field stimulation in a concentration-dependent fashion. Substance P potentiated the response to electrical field stimulation significantly more than

EXAMPLE 9

Effects of Enkephalinase Inhibitors on Bradykinin Induced Airway Smooth Muscle Contraction The methods used were the same as those described in Example 7. Bradykinin (Sigma) and lys-bradykinin (kallidin; Sigma) caused contraction in a dose-dependent fashion (10$^{-11}$ to 10$^{-5}$M) (FIG. 15). In the absence of enkephalinase inhibitors, bradykinin was more potent than lys-bradykinin. Leu-thiorphan (10$^{-6}$M) shifted the dose-response curves to lower concentrations by 1 to 1.5 log units. In the presence of Leu-thiorphan, the contractile effects of bradykinin and lys-bradykinin were equally potent. This study demonstrates that enkephalinase present in airway tissue decreases the effect of kinin-induced smooth muscle contraction.

EXAMPLE 10

Effects of Enkephalinase Inhibitors on Substance P-Induced Ileal Smooth Muscle Contraction Using methods similar to those with ferret airway smooth muscle, described in Example 7, longitudinal ileal smooth muscle was examined. In the control state, in the absence of enkephalinase inhibitors, substance P caused tonic contraction in a dose dependent fashion (FIG. 16). Leu-thiorphan (10$^{-5}$M) shifted the dose response curve to lower concentrations by 1 log unit. This study demonstrates that enkephalinase present in gastrointestinal (ileal) tissue decreases the effect of substance P-induced smooth muscle contraction. neurokinin A and neurokinin B. (DPro$^2$, DTrp$^{7-9}$)substance P ($10^{-5}$M, a specific tachykinin antagonist) inhibited substance P-, and neurokinin A-, and neurokinin B-induced potentiating responses to electrical field stimulation (FIG. 14).

These studies establish that substance P, neurokinin A and neurokinin B cause smooth muscle contraction and they potentiate neurotransmission to airway smooth muscle with different potencies. Enkephalinase present in airways is an important inhibitor of tachykinin-induced effects. The mechanism by which leu-thiorphan potentiates tachykinin-induced effects is most likely by preventing degradation of the peptides by enkephalinase. The sensitivity to hydrolysis of different tachykinins by enkephalinase may be the explanation of the change in rank order of potency in tachykinin-induced effects.

The substance P antagonist, (DPro$^2$, DTrp$^{7,9}$)substance P inhibited electrical field stimulation-induced contraction. suggesting that the effects of tachykinins are mediated via tachykinin receptors because this antagonist is selective for tachykinins (Leander, S. R. et al., Nature 294: 467–469 [1981]).

As shown above, the tachykinin-induced effects in ferret trachea may be mediated by enkephalinase because leu-thiorphan augmented tachykinin-induced effects, whereas other inhibitors of proteinases and peptidases did not. Those inhibitors described above include: captopril, an inhibitor of angiotensin converting enzyme; bestatin, an inhibitor of aminopeptidases; and leupeptin, an inhibitor of serine or thiol proteinases. Furthermore, the effects of leu-thiorphan on tachykinin-induced contractions were concentration-dependent (FIG. 13). suggesting that activity of endogenous enkephalinase is closely related to tachykinin-induced effects.

EXAMPLE 11

Chemotactic Assay

The normal functions of mature neutrophils are chemotaxis, phagocytosis, microbicidal action, and digestion of foreign material. Chemotactic factors are generated at the site of inflammation which attract various immunological cells including neutrophils to that site. The mechanism underlying the chemotactic attraction of neutrophils to the inflammatory site is not fully understood. Enkephalinase has been implicated in the mechanism. Connelly, J. C. et al., Proc. Natl. Acad. Sci. (USA) 82, 8737–8741 (1985). In certain cases of hyperimmune responses abnormal influx of neutrophils and other immune cells may cause additional tissue damage.

Enkephalinase has been found to be bound to the cell membrane of human neutrophils. Connelly, et al., supra. Membrane bound enkephalinase from neutrophils cleaves the chemotactic peptide fMet-Leu-Phe (Id.) Neutrophil degranulation and chemotaxis require cleavage of chemotactic peptides (Smith, R. et al., Fed. Proc. Fed. Am. Soc. Exp. Biol. 44, 576 [1985]) and Aswanikumar, S. et al., Proc. Natl. Acad. Sci. (USA) 73, 2439–2442 [1976]). Thus, it has been suggested that neutrophil membrane bound enkephalinase may be associated with the chemotactic signal by cleaving fMet-Leu Phe in the immediate vicinity of the neutrophil receptor. This degradation would control the local concentration of the chemotactic peptide.

An assay was used to test the effects of enkephalinase on neutrophil chemotaxis. See U.S. patent application Ser. No. 06/707,005 now U.S. Pat. No. 4,714,674. Neutrophils were isolated by sedimentation over dextran from peripheral blood of human donors. A sample of neutrophils is placed over a 5 μm filter in a chemotaxis chamber containing aliquots of test material. Three to six replicates were run for each test for 1 hr. at 37° C. The number of migrating neutrophils in each chamber is then counted. The chemotactic potential is evaluated by the number of cells in five selected unit areas. A commercially available chemotaxis kit, Neuroprobe, Cabin John, Md. was used. Various specific inhibitors of enkephalinase were used to determine the role of enkephalinase in chemotaxis of neutrophils. Chemotactic activity is reported as the total number of neutrophils observed in five fields of the kit membrane under 100× magnification. Thus, the larger the number the more chemotactic was a particular test composition.

TABLE 3

| Chemotactic Activity | |
|---|---|
| | Neutrophil Migration (% control) |
| Formyl Met—Leu—Phe 1 μM | 100 |
| Formyl Met—Leu—Phe + Thiorphan 10 μM | 29 ± 19 (n = 5) |
| Formyl Met—Leu—Phe + Phosphoramidon 10 μM | 65 (n = 1) |

Thus, neutrophil enkephalinase modulates chemotactic activity.

EXAMPLE 11

Enkephalinase Cleavage of Bombesin

Bombesin and bombesin-like peptides have been shown to function as growth factors for airway epithelial cells (Willey et al., supra) and in human small-cell lung cancer (SCLC) (Cuttitta et al., Nature 316: 823–826 [1985]). It was shown that a monoclonal antibody to bombesin inhibited the in vivo growth of SCLC cells in mice. Id.

Bombesin ($10^{-4}$M) and (Leu$^5$)enkephalin ($10^{-4}$M) were added to purified rat kidney enkephalinase (50 ng in 150 ul 50 mM, pH7.4 HEPES buffer containing 0.02% Triton X-100). After 30 minutes at 37° C., 50 μl 2N HCl was added and the incubation medium was analyzed by HPLC (C18 μBondapak column, 30 minute linear gradient from 0 to 75% acetonitrite in 0.1% trifluoroacetic acid). While 15% of the (Leu$^5$) enkephalin was found degraded, as much as 80% of the bombesin was hydrolyzed. Bombesin appears to be a good substrate for enkephalinase. Administration of therapeutically effective amounts of enkephalinase may retard the growth of a tumor requiring bombesin for cellular proliferation.

EXAMPLE 13

In Vivo Studies of the Effects of Enkephalinase on Substance P-Induced Extravasation This study demonstrates that substance P injection increases the extravasation of Evans Blue dye. Pretreatment of animals with enkephalinase reduced those effects.

Male Long Evans rats were used for this study. Each rat (250 gm) was anesthetized by injecting sodium methylhexabarbital (75 mg/kg, ip), and placed in a supine position. Venous cutdowns in the jugular or femoral veins were made for intravascular injections.

Extravasation of Evans Blue dye was measured to study changes in vascular permeability. After intravascular injection, the dye mixes rapidly in the vascular system where it binds to serum albumin, thereby creating a high molecular weight dye-protein complex. The dye-protein complex remains in the vascular system unless blood vessel permeability was increased. Permeability changes were monitored by injecting Evans Blue dye solution (0.250 ml of a 30 mg/ml solution in saline) into the venous circulation. After 1 minute, substance P (1 μg/kg) in saline was injected. Five minutes later, the animal was perfused with a fixative solution consisting of 0.05M citrate buffer (pH 3.5) containing 1% paraformaldehyde for 2 minutes. The acidic fixative prevents the Evans Blue from diffusing out of the tissues. After fixation, the skin of the feet and nose was dissected free from the underlying connective tissue, weighed, and placed in 2.0 ml of formamide (50° C., 24 hours) to extract the dye. The amount of dye extracted from each tissue was determined by measuring the absorbance at 620 nm and comparing the results with a standard curve for known concentrations of dye. The Evans Blue content is expressed as ng dye/gm tissue wet weight.

Preliminary experiments were designed to determine the dose of substance P that caused reproducible, modest responses. Experiments showed that 1 μg/kg was a satisfactory does. Subsequent experiments were designed to determine whether enkephalinase inhibits responses to substance P.

Enkephalinase was purified from rat kidneys using published methods (Malfroy and Schwartz, J. Biol. Chem. [1984]) and was concentrated to 1 mg/ml buffer for use. The buffer consisted of 5 mM HEPES (pH 7.4) containing 0.1% Triton X-100 and 500 mM methyl-α-D-glucopyranoside. The effect of enkephalinase on the responses to substance P was studied by injection of the enzyme (100 μg i.v.) per animal 15 minutes prior to injection substance P.

Results of these experiments are shown in Table 4. These studies demonstrate that substance P increased vascular permeability in the skin of the nose and paws. Studies showed that 1.0 μg/kg of substance P (intravenous) increased the permeability to Evans Blue dye, and that enkephalinase (100 μg) inhibited the vascular responses in the skin in three of four experiments to substance P.

TABLE 4

Effect of Enkephalinase on Vascular Permeability

| Experiment number | Control | Enkephalinase | % Control |
|---|---|---|---|
| Nose | | | |
| Experiment #R-4 | 18.3 ± 1.12* | 12.1 | 66.2 |
| Experiment #R-6 | 58.4 | 30.0 | 51.3 |
| Feet | | | |
| Experiment #R-4 | .9.4 ± 2.7 | 11.1 | 118 |
| Experiment #R-6 | 11.9 | 3.6 | 29.9 |

*Evans Blue Content in ng/gm wet weight

EXAMPLE 14

In Vivo Effects of Enkephalinase on Airflow Resistance

The effects of enkephalinase on airway smooth muscle in vivo, is studied using previously published methods (Holtzman et al. Am. Rev. Respirat. Disease 127: 686 [1983]). Airflow resistance is measured in anesthetized animals (sodium pentobarbital, 30 mg/kg, ip, or chloralose, 40 to 60 mg/kg, iv). An endotracheal tube is inserted into the upper trachea and the animal is ventilated according to its size using a constant volume ventilator. Large animals such as dogs require tidal volumes of 10 ml/kg at a frequency of 30 breaths per minute. Esophageal pressure is measured using a balloon catheter inserted into the middle of the esophagus. The transpulmonary pressure is the difference in pressures between the endotracheal tube and the esophageal catheter. Airflow rates are measured with a sensitive pneumotachograph, and the airflow resistance is calculated by a method of electrical subtraction.

Tachykinins such as substance P are delivered by aerosol, intratracheal instillation, or intravenously. A dose of mediator peptide that increases airflow resistance by approximately two times is used for subsequent studies of airway responsiveness. A comparison of the response to the peptide agonist in the absence and presence of different doses of enkephalinase is made.

EXAMPLE 15

Measurement of Inflammatory Cell Responses In Vivo

Neutrophil chemotaxis, presence of eosinophils and other inflammatory cells, and mast cell degranulation in vivo, is measured in biopsy specimens from airway and other tissues. Tissues are taken from control animals, animals treated with substance P or other endogenous peptide mediators, and from animals pretreated with enkephalinase before or after exposing animals to endogenous peptides. Specimens are fixed in 10% buffered formalin, imbedded in paraffin, and 3 sections 4 mm thick are obtained from each tissue. Sections are stained with hematoxylin-eosin followed by naphthol AS-D chloroacetate esterase. The number of neutrophils or other cells are determined for each section from each biopsy specimen to assess airway inflammation. Cell counts are made at 630×. The volume of epithelium or other tissue is determined using a digitizer (Model 614B; Talos Inc.) to obtain the area and the thickness of the section (4 mm), and data are expressed as the number of cells per volume of tissue.

EXAMPLE 16

Effects of Enkephalinase on Esophageal Smooth Muscle Contraction In Vivo

The contraction of the lower esophageal sphincter in anesthetized animals is measured using modifications of the methods published previously (Reynolds et al., Am. J. Physiol. [Gastrointestinal Physiology] 246: 346 [1984]). A catheter system consisting of two tubes, one for recording pressure and infusion of fluid or drugs, and another for recovery of the fluid in the esophagus is inserted into the esophagus, and water is pumped (flow rate: approximately 0.75 ml/min) through the catheter. The fluid is continuously withdrawn from the esophagus so as to keep the volume of fluid in the esophagus constant, and the esophagus patent. By fixing the lower end of the esophagus to prevent shortening of the longitudinal muscles only circular muscular contractions are recorded The pressure recording catheter is attached to a transducer (e.g., Statham Model P23) and pressure is recorded on a chart recorder.

EXAMPLE 17

Effect of Enkephalinase on Renal Hypertension in Rats

Elevated arterial pressure or hypertension may be caused by renal disease. One type of renal hypertension is due to activation of the renin-angiotensin system. Renin, a proteolytic enzyme produced by the kidney, converts angiotensinogen to the decapeptide, angiotensin I, which in turn is converted to angiotensin II. Angiotensin II is a potent pressor compound and exerts this pressor effect directly on arteriolar smooth muscle. Enkephalinase cleaves angiotensin I, thus preventing its conversion to angiotensin II and thus is likely to be an effective therapeutic in the treatment of renal hypertension.

The effects of enkephalinase on renal hypertension is studied using the following procedure; one renal artery is narrowed producing high concentrations of renin followed by high levels of angiotensin manifested in systemic hypertension.

Systemic blood pressure is monitored by surgically placing a catheter in a femoral artery and bringing the catheter out of the body via the back. This allows the accurate monitoring of blood pressure in unanesthetized and unrestrained animals. The effects of enkephalinase and enkephalinase inhibitors on the arterial blood pressure, the blood levels of renin, angiotensin I and angiotensin II are monitored

EXAMPLE 18

Effect of Enkephalinase on Substance P In the Eye

Substance P-like biological activity or immunoreactivity has been found in various parts of the eye, including the cornea and limbus, iris, ciliary body, and choroid. (Stone, R. A. and Kuwayama, Y., Arch. Ophthalmol. 103:1207 [1985]). Substance P-like activity has been observed in the retina of various animals including the chicken, pigeon, rat, guinea pig, rabbit, dog, cow and monkey (e.g. Stjernschantz, J. et al. J. Neurochemistry 38: 1323-1328 [1982]; Unger, W. G. et al., Exp. Eye Res. 19:367-377 [1981]).

The function of substance P in the eye is not established. It has been suggested that substance P may mediate antidromic vasodilation and neurogenic plasma extravasation as part of the inflammatory response to trauma in the eye (Holmdahl, G. et al. Science 214:1029 [1981]).

The role of substance P in the retina, iridial smooth muscles, ocular circulation and the blood-aqueous barrier, intraocular pressure, formation and outflow of aqueous humor has been reviewed. (Stjernschantz. J. in *Pharmacology of the Eye* ed. Sears, M. L. [Springer-Verlag, 1979]). Substance P has been shown to have marked effects on the sphincter muscle of the iris (Mandahl, A. and Bill. A. Acta. Physiol. Scand. 109:26 [1980]). It has also been shown that the contractile response to nerve stimulation of the rabbit iris sphincter could be antagonized by a substance P analog. These results suggest that substance P or a closely related peptide is specifically involved in this response. (Leander, J. Acta Physiol. Scand 112:185-193 [1981]). In vivo a pupillary block and increased intra-ophthalmic pressure accompanying intense and sustained miosis has been observed following acute injury. (Al-Chadyan, A et al., Invest. Ophthalmol. Vis. Sci. 18: 361-365 [1979]; Stjernschantz, J. et al., Invest. Ophthalmol. Vis. Sci. 20:53-60 [1981]). Thus substance P may be involved in the sustained and intense miosis observed during cataract surgery or in response to acute injury to the eye.

Injection of high doses ($\geq 1$ $\mu$g) of substance P into the anterior chamber of the eye induced an increase in intraophthalmic pressure. (Mandahl. A. and Bill, A., Acta Physiol. Scand. 112:331-338 [1981]; Stjernschantz, J. et al., Invest. Ophthamol. Vis. Sci. 20:53-60 [1981]). Low doses ($\leq 10$ ng) induce mioses but no appreciable increase in intraophthalmic pressure. (Nishiyana, A. et al., Jpn. J. Ophthal. 25:362-369 [1981]).

Since enkephalinase cleaves substance P, administration of enkephalinase either prior to, during or immediately following cataract surgery is likely to prevent the intense miosis and increased ophthalmic pressure. The effects of enkephalinase on the intense miosis and increased ophthalmic pressure may be studied using various opthalmic models in rabbits such as the aphakic rabbit model for studying the effects of topically applied drugs (Mirate, D. J. et al., Curr.Eye Res. 1[8]:491-493 [1981] and Anderson. J. A. et al., Arch. Opthalmol. 100 [4]:642-645 [1982]). Contraction of the pupil and of the iris sphincter muscle as well as intraocular pressure and drug absorption to areas of the eye is monitored during surgery with and without administration of enkephalinase.

We claim:

1. A method of treatment of disorders associated with substance P susceptible to cleavage by enkephalinase comprising administration of a therapeutically effective dose of enkephalinase to an animal affected by such disorder.

2. The method of treatment of claim 1 wherein the disorder is inflammation.

3. The method of treatment of claim 1 wherein the disorder is airway disease.

4. The method of treatment of claim 1 wherein the disorder is increased ophthalmic pressure.

5. The method of treatment of claim 3 wherein the airway disease is asthma.

6. The method of treatment of claim 1 wherein the disorder is a cough.

7. The method of claim 1 wherein the enkephalinase lacks the cytoplasmic and transmembrane domain.

8. The method of claim 1 wherein the enkephalinase lacks the transmembrane domain.

9. The method of claim 1 wherein the enkephalinase lacks the cytoplasmic domain.

10. The method of claim 1 wherein the enkephalinase is unaccompanied by associated native glycosylation.

11. The method of claim 1 wherein the enkephalinase is administered intramuscularly.

12. The method of claim 7 wherein the enkephalinase is administered intravenously.

13. The method of claim 9 wherein the enkephalinase is administered by intrapulmonary inhalation.

14. The method of claim 1 wherein the enkephalinase is administered topically.

15. The method of claim 1 wherein the enkephalinase is administered in a therapeutically effective dose of from about 0.01 mg/kg to about 25 mg/kg.

16. The method of claim 1 wherein the enkephalinase is administered in a therapeutically effective dose of from about 0.1 mg/kg to about 20 mg/kg.

17. The method of treatment of claim 2 wherein the inflammation is allergic dermatitis.

18. The method of claim 1 wherein the condition is contraction of iris sphincter muscles.

* * * * *